(12) United States Patent
Jolly et al.

(10) Patent No.: US 9,550,051 B2
(45) Date of Patent: *Jan. 24, 2017

(54) IMPLANTABLE FLUID DELIVERY APPARATUS AND IMPLANTABLE ELECTRODE

(71) Applicant: MED-EL Elektromedizinische Geraete GmbH, Innsbruck (AT)

(72) Inventors: Claude Jolly, Innsbruck (AT); Ingeborg Hochmair, Axams (AT); Anandhan Dhanasingh, Innsbruck (AT); Pavel Mistrik, Pardubice (CZ); Soeren Schilp, Mieders (AT); Roland Hessler, Innsbruck (AT); Kenneth Mugridge, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

This patent is subject to a terminal disclaimer.

(21) Appl. No.: 15/098,399

(22) Filed: Apr. 14, 2016

(65) Prior Publication Data

US 2016/0220797 A1 Aug. 4, 2016

Related U.S. Application Data

(60) Continuation of application No. 14/507,435, filed on Oct. 6, 2014, which is a continuation of application
(Continued)

(51) Int. Cl.
*A61F 2/18* (2006.01)
*A61M 31/00* (2006.01)
(Continued)

(52) U.S. Cl.
CPC ......... *A61M 31/002* (2013.01); *A61M 5/1454* (2013.01); *A61M 5/14276* (2013.01);
(Continued)

(58) Field of Classification Search
CPC ............ A61M 31/002; A61M 5/14276; A61M 39/0208; A61M 39/0247
(Continued)

(56) References Cited

U.S. PATENT DOCUMENTS

| 5,421,818 A | * | 6/1995 | Arenberg | ................ A61F 11/00 604/20 |
| 6,045,528 A | * | 4/2000 | Arenberg | ............ A61M 1/0084 604/28 |
| 7,044,942 B2 | * | 5/2006 | Jolly | ................ A61M 5/14276 604/891.1 |

* cited by examiner

*Primary Examiner* — Edward Moran
*Assistant Examiner* — Michael Carey
(74) *Attorney, Agent, or Firm* — Sunstein Kann Murphy & Timbers LLP

(57) ABSTRACT

An implantable drug delivery system includes a middle ear section with a proximal end fixed to a tympanic membrane of a patient, and a distal end that penetrates through a fluid-tight sealed opening into the inner ear. An inner ear section has a proximal end that is connected to the distal end of the middle ear guide member at the sealed opening, and a closed distal end terminating the inner ear holding member some predetermined distance within the cochlea. A hollow interior of the inner ear section is configured for containing a replaceable pharmaceutical agent, and an outer surface is configured to release the pharmaceutical agent from the hollow interior into the inner ear of the patient. The middle ear section and the inner ear section are configured to cooperate for replacing the pharmaceutical agent through the proximal end of the middle ear section to the inner ear section.

4 Claims, 22 Drawing Sheets

Related U.S. Application Data

No. 12/906,564, filed on Oct. 18, 2010, now abandoned, which is a continuation of application No. 11/374,505, filed on Mar. 13, 2006, now Pat. No. 7,815,615, which is a division of application No. 10/281,066, filed on Oct. 24, 2002, now Pat. No. 7,044,942.

(60) Provisional application No. 60/336,452, filed on Oct. 24, 2001, provisional application No. 60/394,427, filed on Jul. 8, 2002, provisional application No. 60/394,602, filed on Jul. 9, 2002, provisional application No. 60/417,704, filed on Oct. 10, 2002.

(51) Int. Cl.
*A61M 5/142* (2006.01)
*A61M 39/02* (2006.01)
*A61N 1/05* (2006.01)
*A61N 1/36* (2006.01)
*A61M 5/145* (2006.01)
*A61M 5/168* (2006.01)
*A61M 25/00* (2006.01)
*A61M 39/10* (2006.01)

(52) U.S. Cl.
CPC .... *A61M 5/16813* (2013.01); *A61M 39/0208* (2013.01); *A61M 39/0247* (2013.01); *A61N 1/0541* (2013.01); *A61N 1/36032* (2013.01); *A61M 25/007* (2013.01); *A61M 2039/025* (2013.01); *A61M 2039/0241* (2013.01); *A61M 2039/1072* (2013.01); *A61M 2205/04* (2013.01); *A61M 2205/7518* (2013.01); *A61M 2210/0668* (2013.01)

(58) Field of Classification Search
USPC ............. 600/379; 623/10; 606/109; 607/137
See application file for complete search history.

Example of a refillable reservoir

Example of a self closing promontory valve

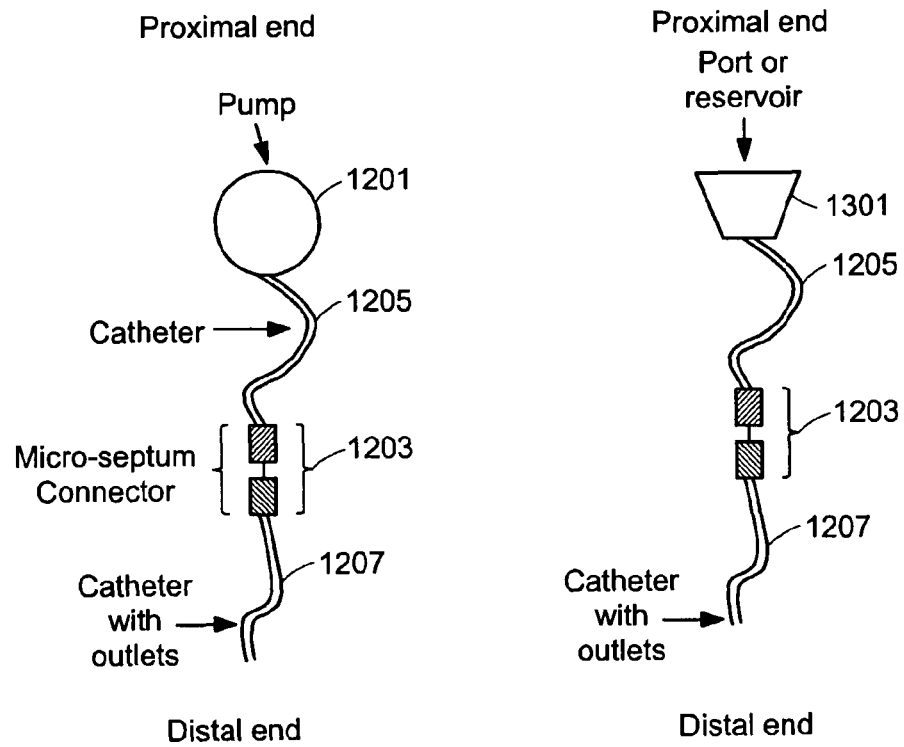
FIG. 12
FIG. 13
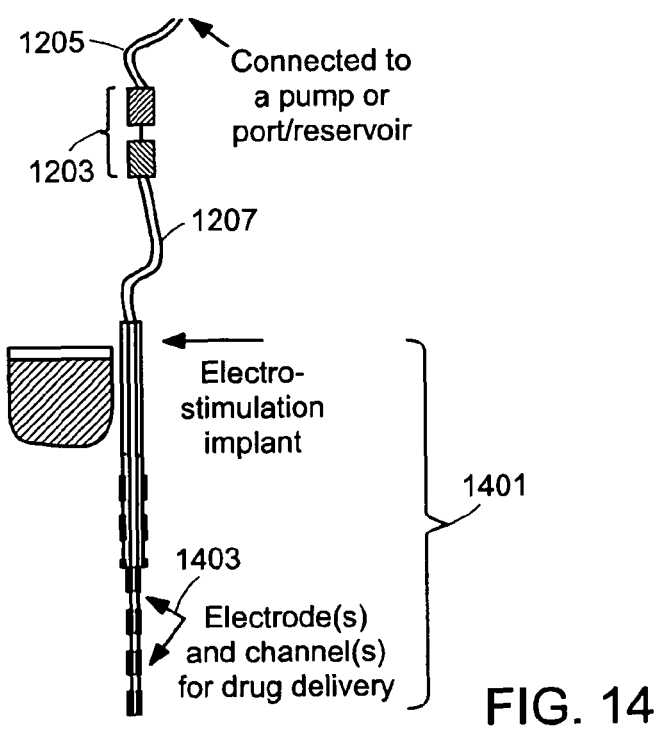
FIG. 14

IMPLANTABLE FLUID DELIVERY APPARATUS AND IMPLANTABLE ELECTRODE

CROSS REFERENCE TO RELATED APPLICATIONS

The present application is a continuation of co-pending U.S. Ser. No. 14/507,435, filed Oct. 6, 2014, published as U.S. Patent Publication 20150025509; which in turn is a continuation of U.S. Ser. No. 12/906,564 filed Oct. 18, 2010, published as U.S. Patent Publication 20110034857, now abandoned; which in turn is a continuation of U.S. Ser. No. 11/374,505 filed Mar. 13, 2006, now U.S. Pat. No. 7,815,615; which in turn is a divisional application of U.S. Ser. No. 10/281,066 filed Oct. 24, 2002, now U.S. Pat. No. 7,044,942; which claims priority to U.S. Provisional Application Ser. No. 60/336,452 filed Oct. 24, 2001; U.S. Provisional Application Ser. No. 60/394,427 filed Jul. 8, 2002; U.S. Provisional Application Ser. No. 60/394,602 filed Jul. 9, 2002; and U.S. Provisional Application Ser. No. 60/417,704 filed Oct. 10, 2002; the disclosures of which are incorporated by reference herein in their entirety.

FIELD OF THE INVENTION

The present invention relates to implantable devices and, more particularly, to implantable fluid delivery apparatuses and an implantable electrodes.

BACKGROUND ART

Fluid delivery systems and devices are often used to provide pharmaceuticals to the body of a human or animal subject. Such systems and devices may employ catheters for fluid delivery. It is also known in the art to implant electrodes and electrical prosthesis in the body to provide electrical stimulation to internal organs and tissue.

For example, intra cochlear electrodes are intended to restore some sense of hearing by direct electrical stimulation of the neural tissue in proximity of an electrode contact. As more and more patients with significant and usable residual hearing are implanted with cochlear implants, it becomes imperative to use a minimally traumatic electrode. In addition, devices may be implanted in a subject when the subject is at a very young age and it may be necessary to re-implant several times during a lifetime. Each consecutive insertion of a cochlear implant may cause trauma to spiral ganglion cells to a minimum. Trauma to spiral ganglion cell is cumulative and cannot be undone in the present state of technology.

To reduce trauma to the organ or tissue, electrodes and catheters should be soft, flexible, and insertion forces should be minimum. Unfortunately, most cochlear implant electrodes on the market today require significant force to be inserted, even for distances which are much less than the full length of the scala tympani.

The required force to insert the electrode or catheter is related to the size, geometry, and the material used in the fabrication of the particular device. Material used in such devices includes materials for wires, contacts, functional metallic or polymer segment, and bulk material. The size of the electrode or catheter, the rigidity of the material used in the electrode or catheter, the hydrophobicity of the outer shell of the electrode array, the energy stored in one way or another in the electrode and the insertion process of the device have an impact on the amount and location of damages that will be inflected to the tissue of the labyrinth during electrode placement. With respect to fluid delivery systems in general, removal and replacement of the system or of particular parts of the system may also cause trauma and damage to living tissue.

Damage and trauma cause bleeding, inflammation, perforation of soft tissue, tears and holes into membranes, and fracture of thin osseous structures. The resulting damage to the inner ear, for example, may cause loss of surviving hair cells, retrograde degeneration of the dendrite which innervates the organ of Corti, and in the worst case, spiral ganglion cell death in the Rosenthal's canal. Cell death means quantitatively less neural tissue is available for stimulation, and qualitatively, that less frequency-tuned fibers are available to represent frequency information. Loss of dendrites without loss of spiral ganglion means that acoustic stimulation is no longer possible, and that no synergetic effects between acoustic and electric stimulation is available. Electro-acoustic synergetic effects may be critical for good sound discrimination in noisy environments.

SUMMARY OF THE INVENTION

Embodiments of the present invention include an implantable drug delivery system having a middle ear section with a proximal end fixed to a tympanic membrane of a patient, a distal end penetrating through a fluid-tight sealed opening into the inner ear, a hollow interior between and connecting the proximal end and the distal end, and an outer surface enclosing the hollow interior and sealed to prevent leakage between the hollow interior and the middle ear of the patient. An inner ear section has a proximal end connected to the distal end of the middle ear guide member at the sealed opening, a closed distal end terminating the inner ear holding member some predetermined distance within the cochlea, a hollow interior configured for containing a replaceable pharmaceutical agent, and an outer surface configured to release the pharmaceutical agent from the hollow interior into the inner ear of the patient. The middle ear section and the inner ear section are configured to cooperate for replacing the pharmaceutical agent through the proximal end of the middle ear section to the inner ear section.

In further specific embodiments, there may also be a micro-valve configured to provide a secure path through the sealed opening. The inner ear section may be made of a polymer matrix material; for example, the inner ear section may be an electrode array of a cochlear implant system.

BRIEF DESCRIPTION OF THE DRAWINGS

FIG. 12 is a graphical illustration of an implantable micro-septum connector configuration for use with a pump and delivery catheter in accordance with another embodiment of the present invention;

FIG. 13 is a graphical illustration of an implantable micro-septum connector configuration for use with a port or reservoir and delivery catheter in accordance with a further embodiment of the invention;

FIG. 14 is a graphical illustration of an implantable micro-septum connector configuration for use with an electronic prosthesis in accordance with another embodiment of the invention;

DETAILED DESCRIPTION OF SPECIFIC EMBODIMENTS

Figure 1:
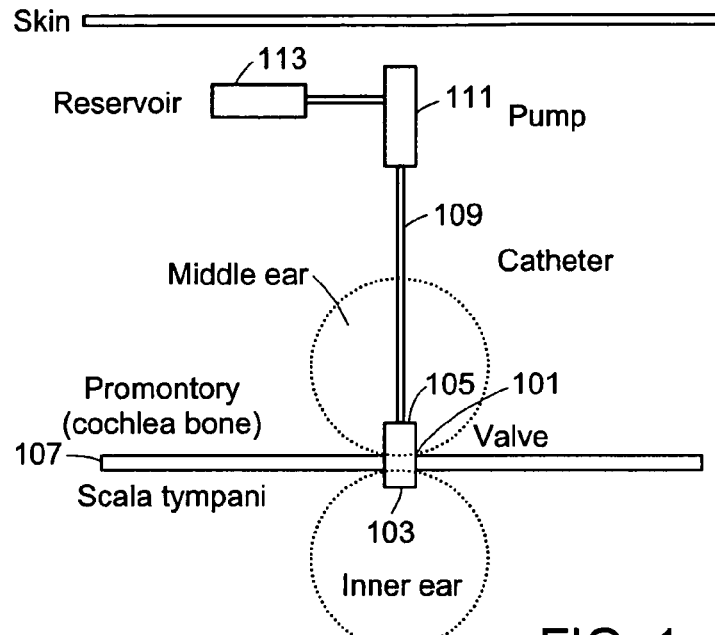
FIG. 1 shows a graphical illustration of a fluid delivery system in accordance with an embodiment of the present invention.

FIG. 1 is a graphical illustration of a fluid delivery system in accordance with an embodiment of the present invention. For purposes of this embodiment, the fluid delivery system is employed to deliver pharmaceuticals to, for example, the inner ear of a subject. However, the fluid delivery systems and apparatuses described herein may be used to deliver many different types of fluids to one or more internal areas of a subject's body. The system shown in FIG. 1 includes a biocompatible and sealed micro-valve 101 with an inner ear side 103 and a middle ear side 105. The micro-valve 101 provides a secure path between the middle ear and the inner ear through the promontory bone 107 of the cochlea or through the round window. The connection may, for example, be to the scala tympani, vestibuli or scala media. The micro-valve 101 provides permanent access to the inner ear for fluid delivery of various viscosity and healing functions. The micro-valve 101 may be made of, for example, polymer, titanium (precision cut by laser micro-machining as can be produced by Kurtz G.m.b.H., Germany), nickel-titanium alloy or any combination of biomaterial. For use in the inner ear, the micro-valve 101 may be anchored on the cochlea promontory bone 107. Similarly, the micro-valve may be located in the round window or semicircular canal of the inner ear. The anchoring and sealing between the metallic and/or polymer based micro-valve 101 and the promontory bone 107 is accomplished through use of, for example, a biocompatible cement, and/or a mechanical fitting in a treaded shaft, and by osteo-integration. The connection between the micro-valve 101 and the promontory bone 107 may be, for example, through a tube with an inner and outer thread. The micro-valve 101 may be removable from the promontory bone 107 if and when necessary.

Figure 4:
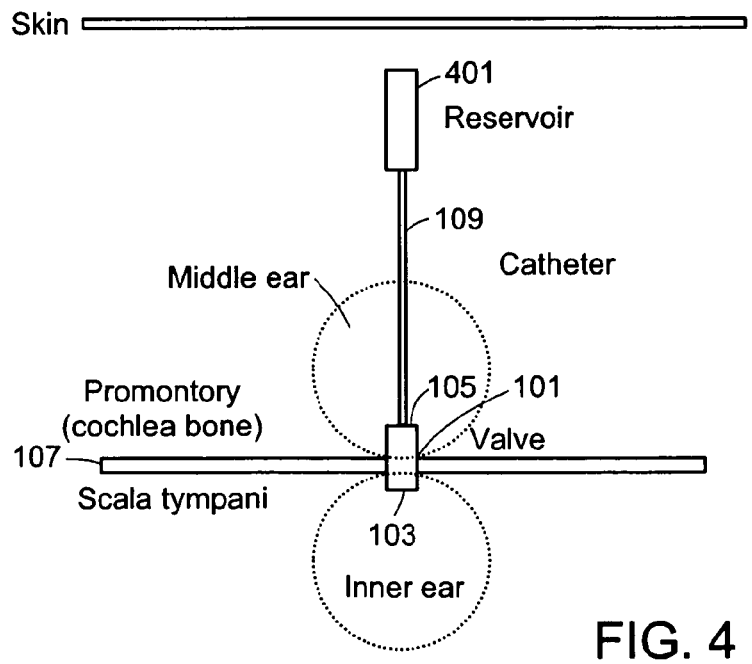
FIG. 4 is a graphical illustration of a fluid delivery system in accordance with a further embodiment of the invention.
Figure 10:
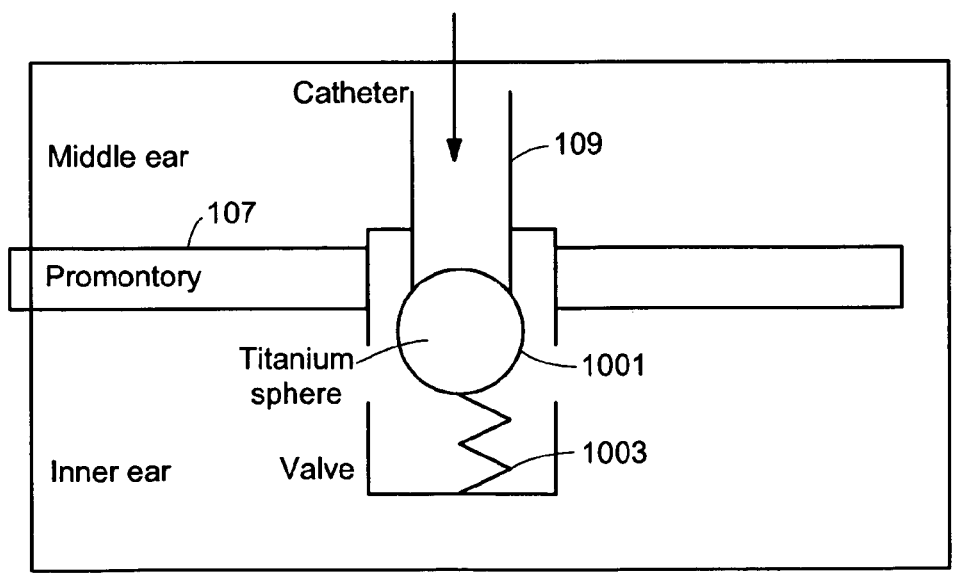
FIG. 10 is a graphical illustration of a self-closing valve in accordance with a further embodiment of the invention.

The placement of the micro-valve 101 typically, but not necessarily, requires drilling a hole approximately 0.8 to 2 mm or more in diameter on the promontory bone. The micro-valve 101 may be self-closing, as shown in FIG. 10, when no fluid pressure is sensed through the catheter, reservoir or pump. The micro-valve 101 may be surface coated, or treated by chemical vapor deposition or other means to prevent tissue growth and occlusion of the valve orifice over time in the intra-cochlea region. The micro-valve 101 may also include a magnet, and a magnetic control system through a tympanoplasty. Fluid delivery to the micro-valve 101 may be accomplished through a flexible catheter 109 that may be, but is not limited to, 0.5 to 2 mm in inner diameter. One end of the catheter 109 may be securely connected, for example, to the middle ear side 105 of the micro-valve 101. The connection is sufficiently tight to prevent fluid leakage from the catheter to the middle ear. The connection may be permanent or disconnectable through a surgical approach. The catheter 109 inner surface may be treated to impart hydrophilic properties to the lumen, as hydrophilic properties are favorable to the delivery of viscous fluid. The other end of the catheter may be connected to a fluid source such as a pump 111 with reservoir 113. Similarly, the fluid source may comprise a reservoir 401 with a passive unloading system such as a spring activated piston or a piston which includes a magnet and is operated by magnetic forces from the exterior or interior as shown in FIG. 4. The catheter 109 may also be connected to an osmotic pump. The pump 111 may be active, which means it may be operated by energy transferred transcutaneously to an electronic control box such as the one used with a cochlear implant or other implantable prosthesis. The pump 111 may also be passive with energy transfer by, for example, a gas or other fluid loaded in a chamber of the pump.

When energy is delivered to the pump 111 to move fluid from the reservoir 113 down the catheter to the inner ear or when the fluid is moved via a spring loaded reservoir 401, the pressure is sufficient to open the micro-valve 101. When no energy or pressure is sensed by the micro-valve 101, the micro-valve 101 may close automatically, thereby sealing the inner from the middle ear. The micro-valve 101 closure may take place through the use of a titanium sphere 1001 attached to a spring 1003 on the inner ear side of the valve as shown in FIG. 10. However, other methodologies for opening and closing the micro-valve 101, such as fluid pressure or piezoelectrics, may be used.

Figure 6:
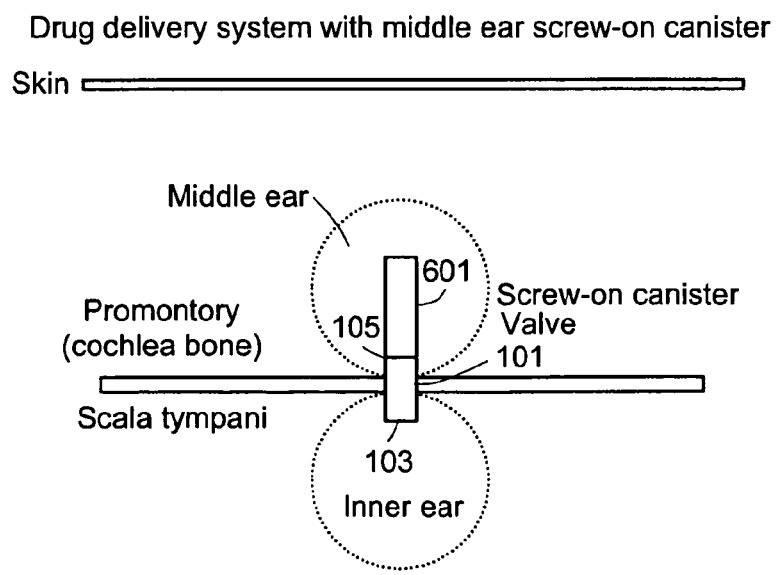
FIG. 6 is a graphical illustration of a fluid delivery system having a fluid canister in accordance with an embodiment of the invention.

In another embodiment of the invention, the micro-valve 101 may be securely connected directly to a screw-on canister 601 as shown in FIG. 6. This allows for one-time fluid delivery. The canister 601 may be removed and refilled or replaced by another canister with a passive fluid delivery function.

Figure 2:
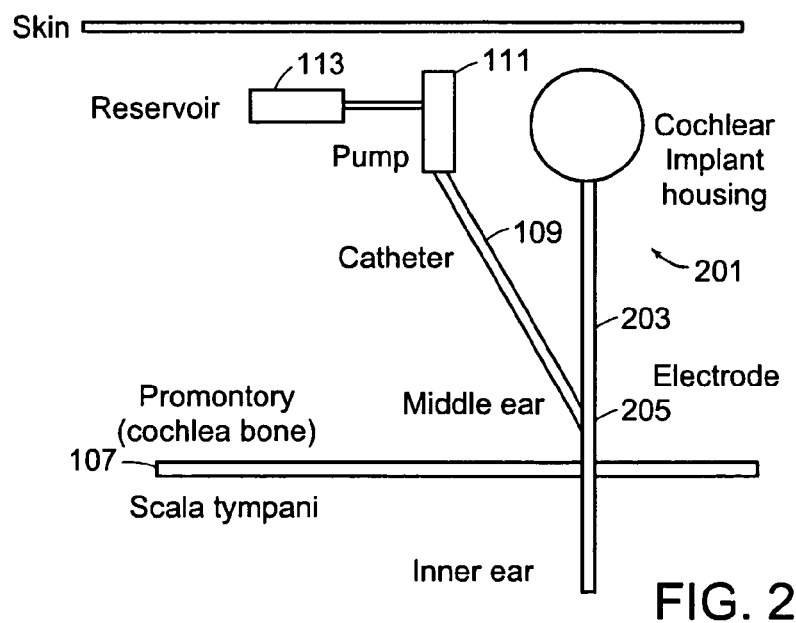
FIG. 2 is a graphical illustration of a fluid delivery system fused to a cochlear implant in accordance with another embodiment of the invention.

As noted above, fluid delivery systems in accordance with the invention may be used in combination with an electronic prosthesis or implant, for example, a cochlear implant. This may be accomplished in two ways: fusion of the catheter and an electrode associated with the prosthesis or implant, or parallel delivery of fluid and electrical current to the body. FIG. 2 is a graphical illustration of a fluid delivery system fused to a cochlear implant in accordance with an embodiment of the invention. A catheter 109 of the fluid delivery system is connected to a cochlear implant 201 via its electrode 203. The electrode 203 is hollow over a length which starts at a catheter and electrode junction 205. (Note that a valve as described above may also be used with this embodiment.) The hollow part of the electrode 203 may continue in length to somewhere intra-cochlea. The hollow electrode 203 acts as a pathway for fluid delivery to the inner ear. On the intra-cochlea section of the electrode one or several channels of adequate size built in the electrode 203 material permit access to the fluid of the inner ear. The catheter 109 which connects a fluid source to the implant may or may not be disconnectable from the electrode 203. When not disconnectable, a valve or switch (not shown) prevents any connection between the inner ear and the other structures of the temporal bone, including the middle ear (fluid, tissue or air).

Figure 3:
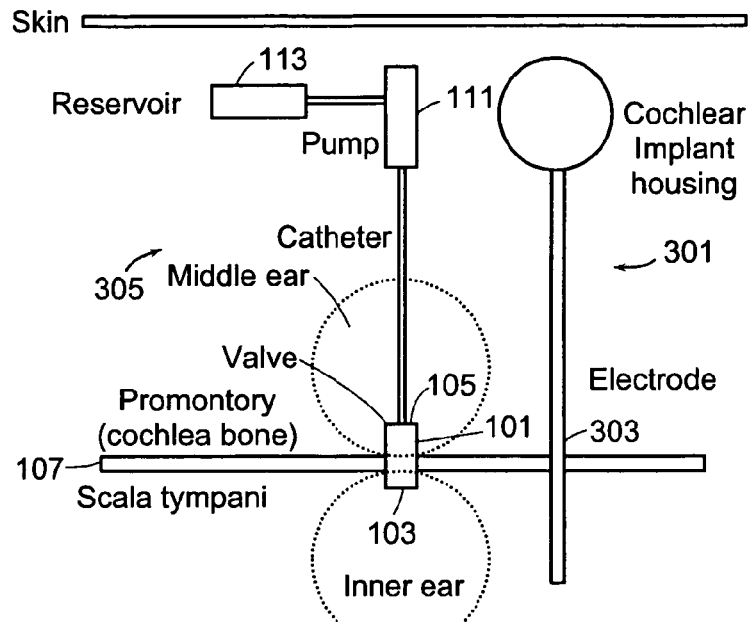
FIG. 3 is a graphical illustration of a fluid delivery system implanted parallel to a cochlear implant in accordance with an embodiment of the invention.

FIG. 3 is a graphical illustration of a fluid delivery system implanted parallel to a cochlear implant in accordance with an embodiment of the invention. Parallel delivery means that the cochlear implant 301 and the fluid delivery system 305 are not fused. A single large cochleostomy or two separate but adjacent cochleostomies may be used to accommodate the separate leads of the electrode 303 and the fluid delivery system 305. The cochleostomy (ies) may be next to each other on the promontory bone. In this case the cochlear implant electrode 303 and fluid delivery system 305 may be introduced in the inner ear through the classical surgery which includes a posterior tympanatomy or one enlarged cochleostomy allowing both electrode and fluid delivery through the same or adjacent promontory bone opening. A typical approach requires that two cochleostomies be drilled after two separate surgical approaches to the promontory bone. The first surgical approach is the classical posterior tympanatomy. The second surgical approach is a variant of the so-called supra-meatal approach that has been described by Prof. Kronenberg, Prof. Häusler, and Dr. Kiratzidis. The electrode or fluid delivery system may be inserted in the classic cochleostomy following posterior tympanotomy. The electrode or fluid delivery system may be inserted in a cochleostomy following the suprameatal approach. The electrode or fluid delivery system may also be implanted through the round window. All permutations of electrode and fluid delivery system are possible with the two cochleostomies or one cochleostomy and the round window opening.

Figure 5:
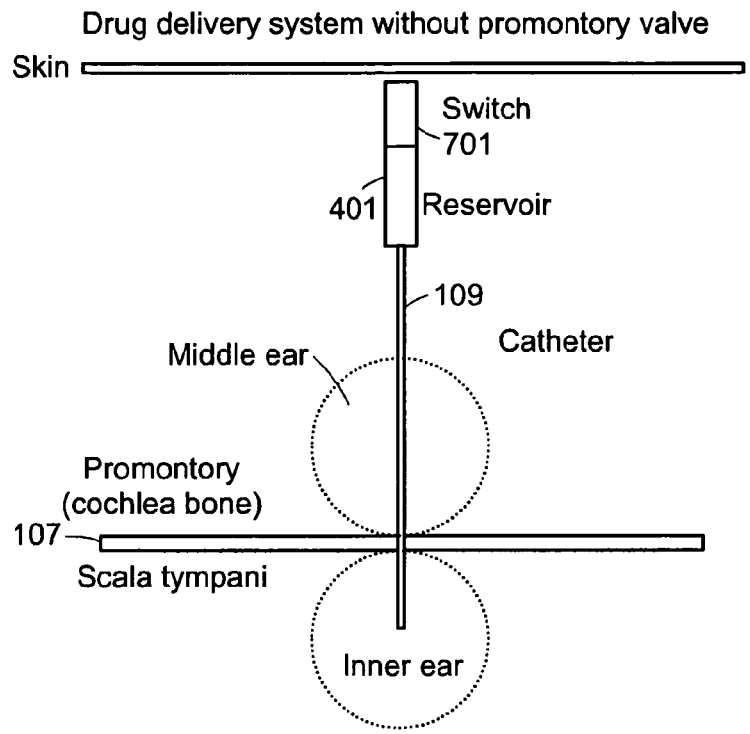
FIG. 5 is a graphical illustration of a fluid delivery system in accordance with another embodiment of the invention.
Figure 7:
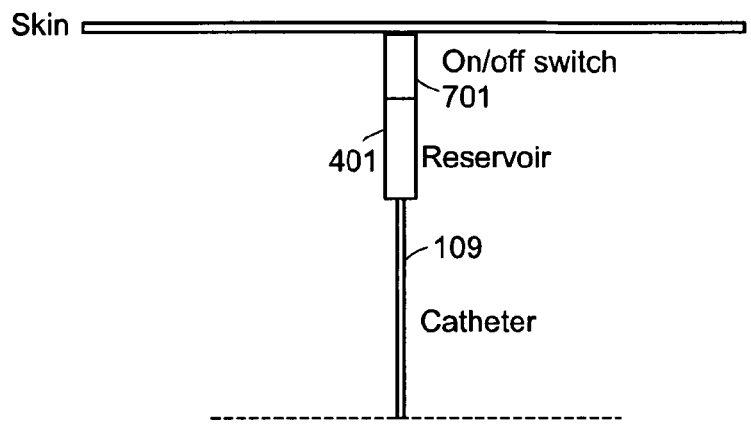
FIG. 7 is a graphical illustration of a switch that may be implanted under the skin in accordance with the embodiments of FIGS. 1-5.
Figure 8:
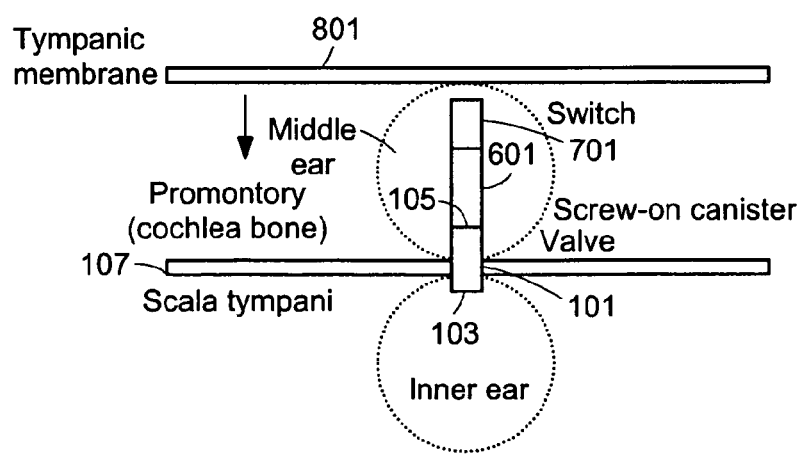
FIG. 8 is a graphical illustration of a switch that may be implanted in the middle ear of a subject in accordance with the embodiments of FIG. 5.

FIG. 5 is a graphical illustration of a fluid delivery system in accordance with another embodiment of the invention. In accordance with this embodiment, the catheter may be inserted directly in the inner ear without a promontory valve present. In this case a cochleostomy is drilled and the catheter is inserted a certain distance in the opening. The catheter may be securely sealed with fibrin glue (for example) on the promontory bone. FIG. 7 is a graphical illustration of a switch that may be implanted under the skin in accordance with embodiments of the invention. In the various embodiments (reservoir with piston, reservoir and pump, screw on canister, refillable and non-refillable reservoir, reservoir incorporated with a cochlear implant system, drug delivery system with or without valve on the promontory, etc.) a provision may be incorporated to stop fluid flow at any time during fluid delivery if the patient should suffer side effect. Fluid flow may be stopped, for example, through telemetry when a pump with a telemetry receiver is included in the design. Fluid may also be stopped by a passive on/off mechanical switch 701. Such an on/off switch 701 may be incorporated on the catheter, on the reservoir, or on the valve, for example. The switch 701 may be activated on or off manually when reachable from the outside (if located at the surface of the skull just underneath the skin for example). The switch 701 may also be activated through a magnetic energy transmitted transcutaneously or through the tympanic membrane 801, shown in FIG. 8. The switch may also be activated on or off through a small opening on the tympanic membrane (tympanoplasty) followed by insertion of a specially designed tool in the valve or on a specially located switch in the middle ear close to the valve. The specially located switch may be a metallic part overhanging the promontory and accessible through a tympanoplasty.

Figure 9:
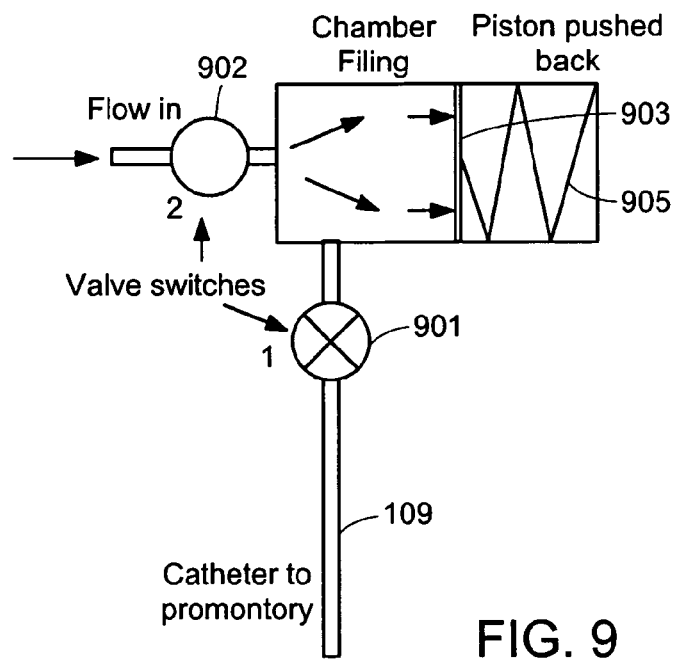
FIG. 9 is a graphical illustration of a refillable reservoir in accordance with another embodiment of the invention.

In accordance with various embodiments of the drug delivery system, the reservoir or canister may be refillable. FIG. 9 illustrates that refilling may take place, for example, through injection of the therapeutic fluid through a thick impermeable membrane located on top of the reservoir, or through a special outlet valve. Such refilling can take place following a local anesthesia, and after incision of the skin covering the reservoir. Refilling may also take place through a small incision on the tympanic membrane and the introduction of a needle in a receptacle on the reservoir. When the delivery system is a spring loaded reservoir, for example, a valve switch system may be used to refill the reservoir. After access to the apparatus, valve switch 901 is closed and valve switch 902 is open. Fluid may be injected through the switch valve 902 with a needle for example, thereby pushing piston 903 back and loading the pump fluid and compressing the spring 905.

Figure 11:
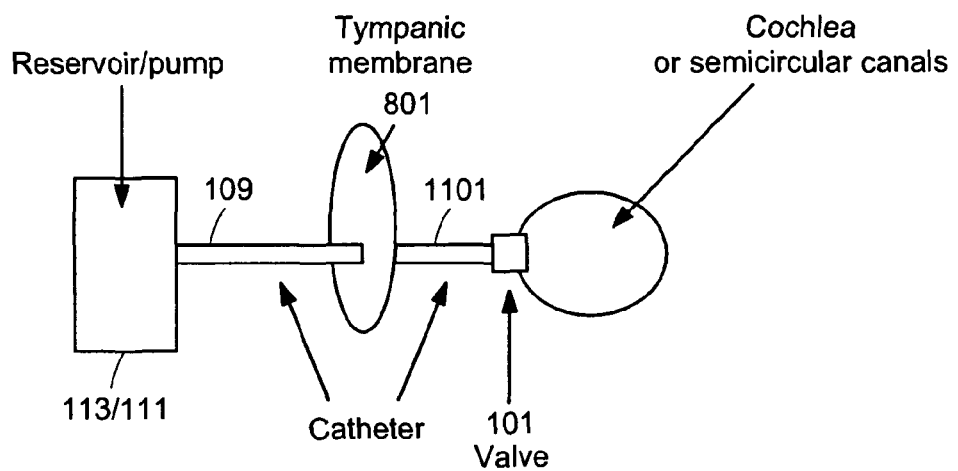
FIG. 11 is a graphical illustration of a fluid delivery system for delivery of fluid to the inner ear of a subject in accordance with another embodiment of the invention.

FIG. 11 is a graphical illustration of a fluid delivery system for delivery of fluid through the tympanic membrane of a subject. Here, the pump and/or reservoir 111, 113 is located outside the outer ear, and a catheter traverses the outer ear and the tympanic membrane. A segment of the catheter 1101 in the middle ear connects to a valve located on the promontory bone, round window or oval window. The catheter 1101 connection may be disconnectable by pulling back on the catheter tube and causing a force from the middle ear toward the outer ear. As in the embodiments described above, the pump/reservoir may comprise and on/off switch and the reservoir may be refillable. FIGS. 12-14 illustrate another device for delivering fluid to the body of a subject. The device includes a fluid source, such as a fluid pump 1201 (as shown in FIG. 12) or a fluid port or fluid reservoir 1301 (as shown in FIG. 13). The device further includes a micro-septum connector 1203. The micro-septum connector is in fluid communication with a spear catheter 1205 at a proximal end which, in turn, is in fluid communication with the fluid source. The micro-septum connector 1203 is also in fluid communication with a port catheter 1207 at a distal end. The port catheter 1207 may be in fluid communication with another catheter (not shown) or with one or more electrodes or electronic prostheses 1401, as shown in FIG. 14. Each electrode or electronic prostheses 1401 may have one or more fluid channels 1403 with outlets such that each electrode or electronic prosthesis 1401 acts in part as a catheter having one or more outlets.

As described above, the micro-septum connector 1203 is in fluid communication with an implantable fluid pump, a fluid port or reservoir, or an osmotic pump via a spear catheter 1205 and in fluid communication with the body of the subject via a port catheter 1207 which may be connected to or in fluid communication with another catheter or an electrode or electronic prosthesis (such as 1401). The fluid delivery device (such as the port catheter 1207 and electrode or electronic prostheses 1401) and the device that drives and delivers the fluid (such as the fluid pump 1201 or fluid port 1301) are designed to be implanted in a human subject or an animal subject in the course of a surgical procedure. The connection between the two devices is accomplished with the micro-septum connector 1203.

Figure 15:
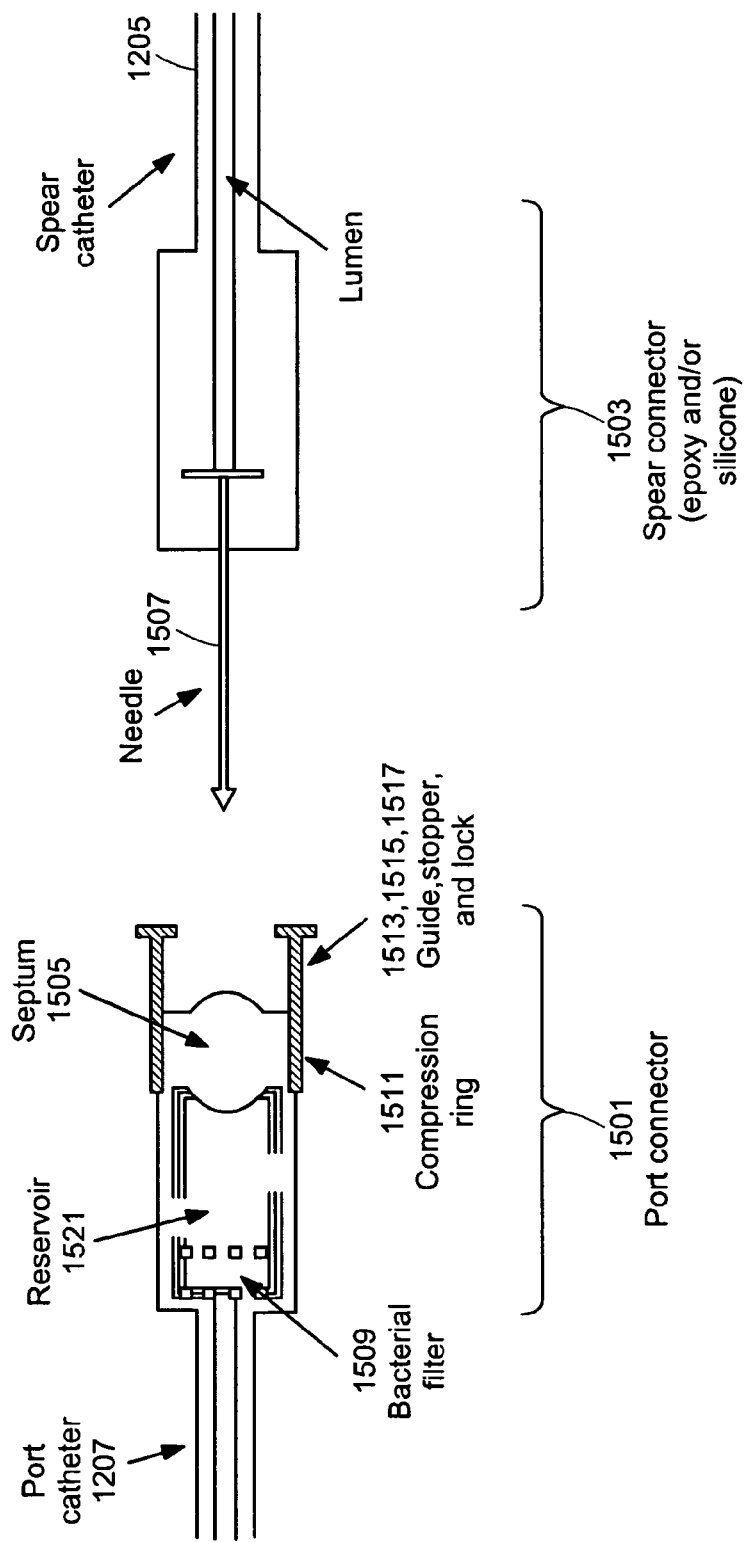
FIG. 15 is a graphical illustration of a micro-septum connector before connection of an implantable port connector and an implantable spear connector in accordance with the embodiments of FIGS. 12-14.

FIG. 15 is a graphical illustration of a micro-septum connector according to an embodiment of the invention. The micro-septum connector comprises an implantable port connector 1501 and an implantable spear connector 1503 (shown unconnected in FIG. 15 and connected in FIG. 16). The implantable port connector 1501 includes a septum 1505 and may be in fluid communication with the port catheter 1207 which transports fluid to a specific location in the subject's body at its distal end. (When in fluid communication with the port catheter 1207, the port connector 1501 is located at the proximal end of the port catheter 1207 as shown if FIGS. 12-14.) The distal end of the port catheter 1207 may have one or more openings to allow fluid to disseminate in the surrounding biological tissue. The spear connector 1503 includes a needle 1507 and may be in fluid communication with the spear catheter 1205 at its distal end. Toward the proximal end of the spear catheter 1205 a fluid source is attached.

Figure 16:
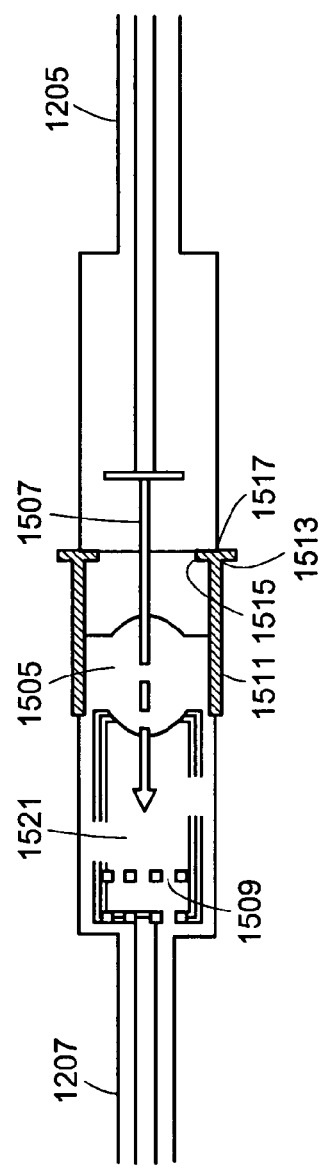
FIG. 16 is a graphical illustration of a micro-septum connector after connection of the implantable port connector and the implantable spear connector in accordance with the embodiment of FIG. 15.

In one embodiment of the invention, the proximal end of the port connector 1501 and distal end of the spear connector 1503 do not join surface to surface. This is to prevent the creation of dead space between the flat surfaces of the micro-septum connector 1203 when joining the port connector 1501 and spear connector 1503 via the needle 1507. In such an embodiment, the needle 1507 of the spear connector 1503 traverses the septum 1505, but a remaining part of the needle 1507, anterior to the septum 1505, is exposed to body fluid and body tissue. Such a situation promotes a good tissue seal at the point where the needle 1507 enters the septum 1505. In addition, the encapsulating tissue is irrigated by the surrounding tissue and can respond well to any inflammation. It is also feasible to introduce tissue, fascia or muscle through the needle 1507 up to the flat end of the spear connector 1503. Introduction of tissue will promote good healthy tissue growth between the flat ends of the port connector 1501 and spear connector 1503. As can be seen in FIG. 16, once joined, the port connector 1501 and the spear connector 1503 permit safe fluid transport without leakage to the surrounding biological environment.

An important feature of the port connector 1501 is the septum 1505. The septum 1505 is made preferably of rubber silicone. The port connector 1501 may also include a compression ring 1511. The compression ring 1511 (or other compression device) compresses the silicone to impart septum properties to the device. The compression ring 1511 is preferably made of medical grade titanium, however, any other material that can compress the silicone in a cylindrical part may be used. Such materials may include shape memory nitinol metal and memory shape polymer. The compression ring 1511 may be terminated toward the connecting side of the port connector 1501 by a guide or a guide mechanism 1513, stopper or other stopping device 1515 and locking mechanism 1517. A bacterial filter 1509 may or may not be placed between the port connector 1501 and the port catheter 1207. The port connector 1501 may also include a reservoir 1521 which may be lined with titanium shell or a titanium shell to prevent piercing by the needle 1507. The proximal end of the port catheter 1207 may optionally be silicone bonded with the port connector. A layer of silicone may be deposited on the entire port connector 1501 to prevent exposure of metal to the environment, and favor encapsulation. Deposition may be accomplished by dip coating the port connector 1501 in the appropriate silicone rubber solution.

The spear connector 1503 may be made of silicone or epoxy or any other bio compatible material as deemed necessary or profitable to the invention. A medical needle (such as 1507) of appropriate size, material, and shape is inserted in a mold such that both ends of the needle protrude out of the mold. Injection molding of silicone and/or medical grade epoxy solidly encases the core of the needle. A catheter (such as the spear catheter 1205) is introduced on one end of the needle and silicone is added and cured to seal the spear connector. The needle 1507 may be slanted and sharp on the side that will pierce the septum 1505. Note that the hole on the needle 1507 that will transfer fluid may be at the end of the needle or may be on the side of the needle at a short distance from the tip. As noted above, the micro-septum connector 1203 may also include a guide or guiding mechanism (such as 1513) to line up the needle 1507 and the port connector 1501 before piercing of the septum 1505 by the needle 1507. The guide or guiding mechanism 1513 permits the lining up of the tip of the needle 1507 with the center of the septum 1505. The guide or guiding mechanism 1513 also prevents large deviation of the needle 1507 upward or downward or sideways. Such deviation could lodge the tip of the needle 1507 in the internal wall of the port connector 1501 and prevent fluid flow.

The stopper or stopping device 1515 may be used to prevent the fusion of the spear connector 1503 and the port connector 1501 on their flat surfaces. The stopper or stopping device 1515 permits a section of the needle 1507 to be exposed to the body fluid even at full insertion. The stopper or stopping device 1515 consequently prevents the creation of a dead space between the flat surfaces of the implantable port and spear connector ends when connected (unless such a flat connection is profitable to the invention by, for example, having an antibiotic coating to prevent formation of a nidus of infection at all time).

The locking mechanism 1517 may be included in the micro-septum connector 1203 to promote the stability of the micro-septum connector 1203 under normal body movement and usage stress. The locking mechanism 1517 may be reversible to allow for replacement of one or more of the parts described above.

Once fabricated and sterilized by appropriate means, a surgeon may join the port connector 1501 and the spear connector 1503 by introducing the needle 1507 through the septum 1505 and, optionally, locking the micro-septum connector 1203 with the locking mechanism 1517. Before joining the port connector 1501 to the spear connector 1503, each may be filled separately with a fluidic pharmaceutical agent. Separate filling allows good priming of the implantable connectors 1501 and 1503 before connection. Filling of the spear catheter 1205 may be accomplished by filling the pump (usually though a pump septum), port with septum and reservoir, or osmotic pump. It may also be that the implantable connectors 1501 and 1503 are connected before any filling and priming of the devices takes place.

If removal and replacement of one or both of the implantable connectors 1501 and 1503 is desired, surgical intervention may include careful removal of tissue growth and membrane encapsulation around the port connector 1501 and removal of the spear connector 1503 by pulling back on one or the other connectors. At this stage either or both of the port connector 1501 and spear connector 1503 may be positioned in the biological environment of interest. This may be done after priming the system in the usual fashion described above. Once replaced and positioned, connection of the port and spear to connectors is accomplished by engaging the port connector 1501 and spear connector 1503 (perhaps by employing the guide 1513), piercing the septum 1505, and, if desired, locking the mechanisms via the locking mechanism 1517.

Figure 17:
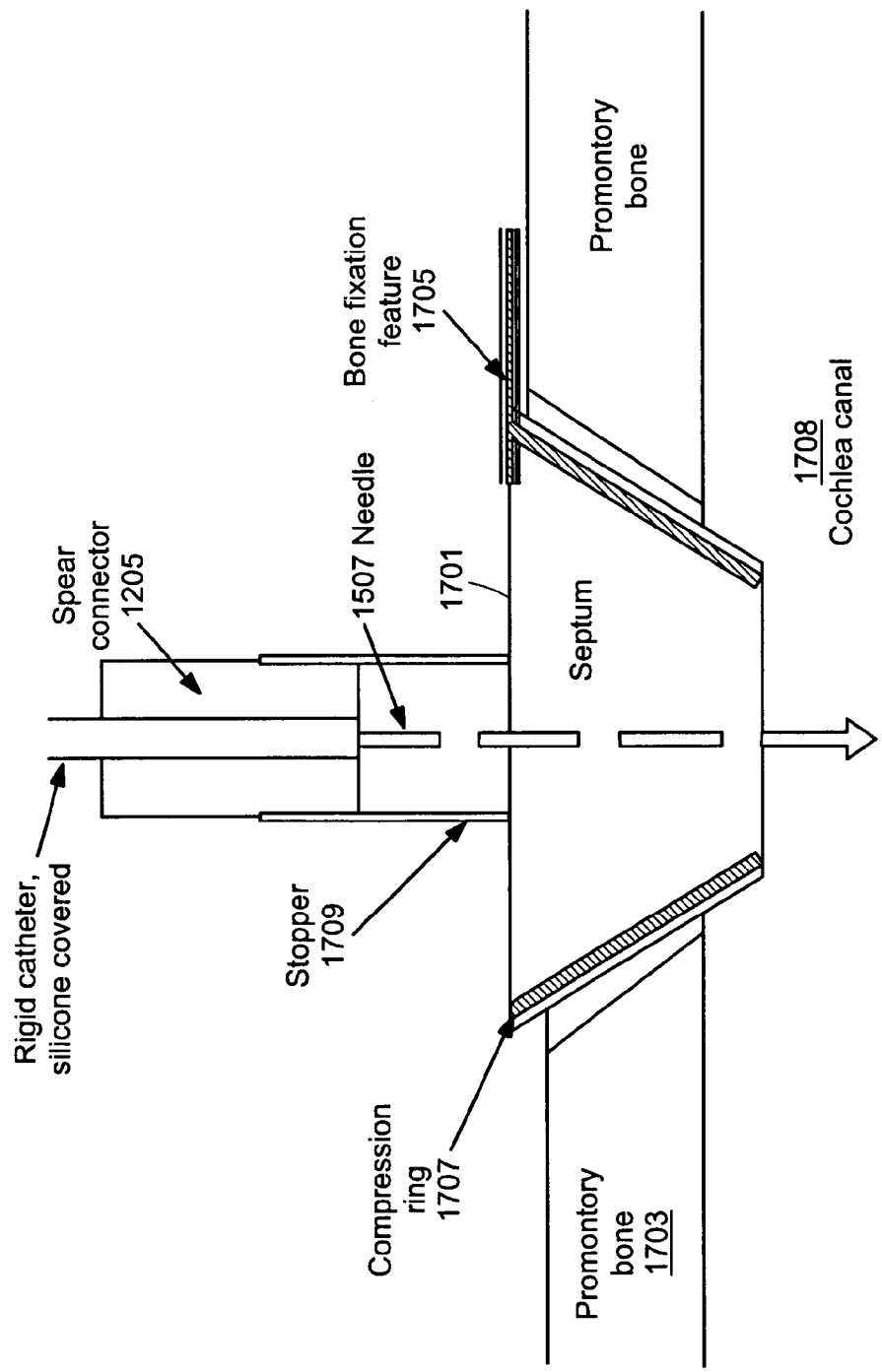
FIG. 17 is a graphical illustration of an apparatus for delivering fluid to the inner ear of a subject in accordance with a further embodiment of the invention.

The system described with respect to FIGS. 12-16 may be used to provide fluid to the inner ear of a subject. FIG. 17 is a graphical illustration of an apparatus for delivering fluid to the inner ear of a subject in accordance with a further embodiment of the invention. The inner ear comprises the cochlea and the semicircular canals (not shown). Fluid delivery may be accomplished through an electrode of a cochlear implant, if so desired, or through a reinforced fluid delivery catheter for partial and full insertion into the inner ear, or through a catheter just apposed against the round window membrane. When such an application is desired, a bony recess may be formed on the surface of the skull to partially bury the connector assembly. Burying the connector prevents protrusion of the connector under the scalp.

In accordance with the embodiment of FIG. 17, a spear connector 1205 and needle 1507 are used to provide fluid to a septum 1701. The septum 1701 may be of appropriate size and shape to be embedded in the inner ear of a subject or on the promontory bone 1703 following surgery. A metal flap or a facial recess may be employed as a bone fixation feature 1705 in order to fix the septum 1701 to the inner ear or the promontory bone 1703. For example, after drilling the promontory bone 1703 with a 2 mm or smaller bore, a conical bed may be made in the bone. A simple conical septum (such as 1701) may be lodged at the opening of the cochlea canal 1708 and anchored on the promontory bone 1703 of the cochlea. The septum 1701 will then remain available for fluid delivery via connection with the spear connector 1205. In such a configuration, the semicircular canal (including the utricle) may be accessible for fluid delivery. Additionally, the configuration of FIG. 17 may also include a compression ring 1707 and stopper 1709 for the purposes explained with respect to the embodiments above.

The fluid delivery systems of FIGS. 12-17 can be easily and quickly connected with a connector. Connections may be long term and leak proof and the fluid delivery systems can be easily disconnected. Upon disconnection, the port catheter may remain sealed, and the fluid delivery systems may be reconnected with a different or with the same fluid driver. The port catheter may remain implanted for use years later while the driver is explanted. If the device is used with an electrode, the electrode does not need to be removed if the fluid driver is taken out. In addition the fluid driver may be reconnected to the electrode at a later date. Fluid delivery modules may be connected in parallel to a single port catheter if so deigned.

Figure 18:
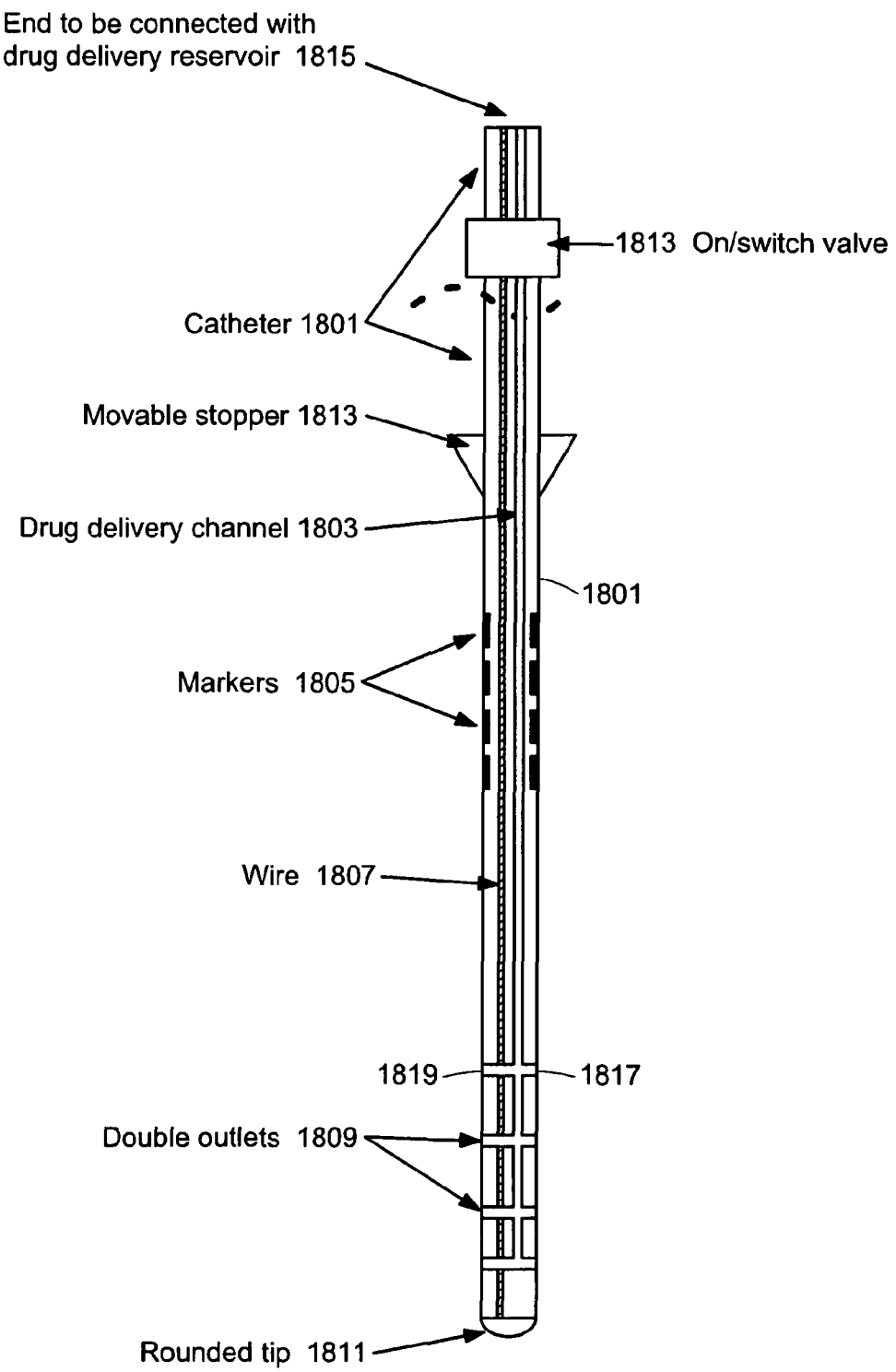
FIG. 18 is a graphical illustration of a catheter in accordance with another embodiment of the invention.
Figure 19:
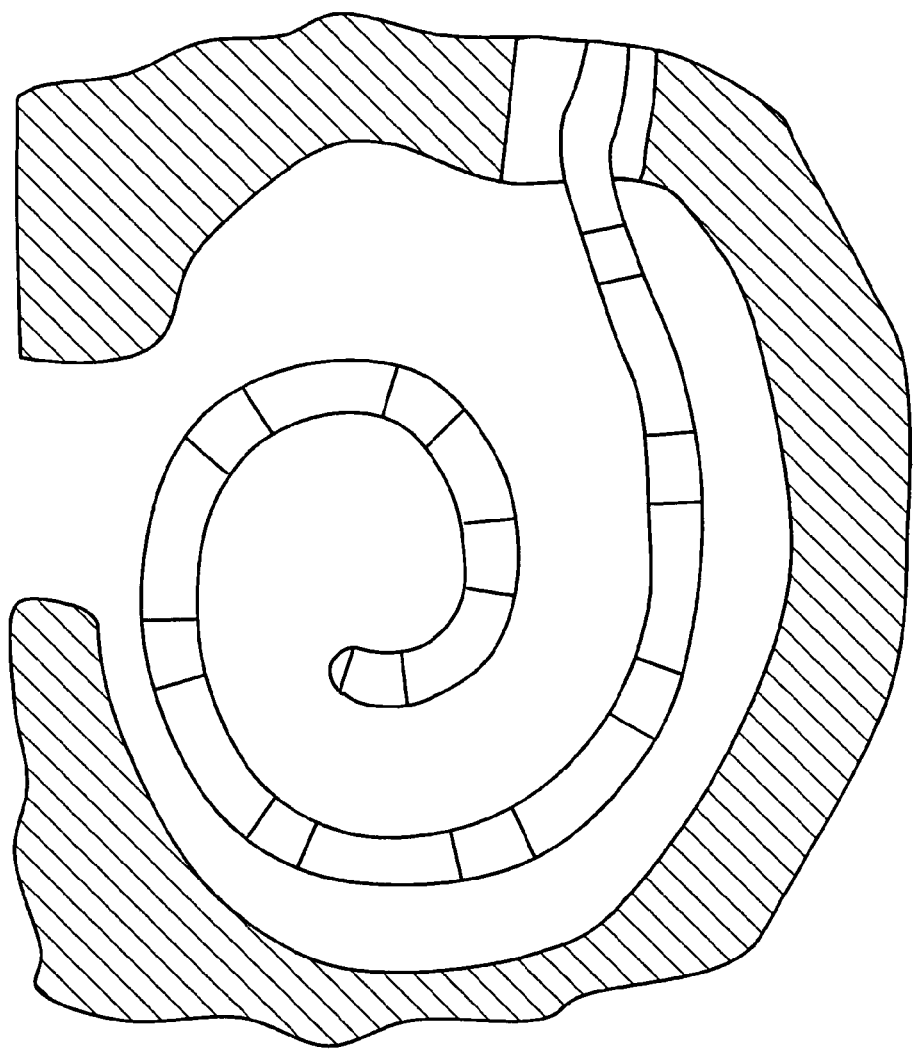
FIG. 19 is a pictorial illustration of the catheter of FIG. 18 implanted in the ear of a subject.

FIGS. 18 and 19 illustrate a catheter in accordance with another embodiment of the invention. The catheter 1801 is designed to be partially or fully inserted in the body of a subject. For example, the catheter 1801 may be inserted in the inner ear (scala tympani, scala vestibuli, or semicircular canals) through a cochleostomy and to deliver pharmaceutical agents to the fluid of the inner ear. Atraumatic insertion of the catheter 1801 depends on the mechanical properties of the catheter. Mechanical properties must be such that an atraumatic insertion around the curvature of the scalae is possible.

The catheter 1801 may be conical or cylindrical in shape, round or elliptical in cross section and may have a rounded tip 1811 for ease of implantation. The catheter 1801 may be polymer based, and the polymer may include silicone, for good flexibility. Alternatively, the catheter may be made of a biodegradable polymer. Similarly, the catheter 1801 may be made of a material which shrinks when stretched.

The catheter 1801 may optionally include one or more reinforcing wires and/or ribbons 1807 made of hard polymer filament or metal or metal alloy to increase the pushability of the device and enhance implantation. The catheter 1801 may also include markers 1805 on the surface of the polymer to indicate insertion depth and/or an adjustable blocker to close the cochleostomy through which it is inserted. Embodiments of the catheter 1801 include double outlets 1809 to provide free flow in the fluid, and these outlets 1809 may be in opposite directions. Similarly, the catheter 1801 may include more than one channel 1803, 1817, 1819 in the center (or toward edges) of the catheter body to control a fluid or drug concentration-distribution profile. The catheter 1801 may also include a lubricating coating to enhance insertion. Similarly, the catheter 1801 may be coated with cortico steroid and/or antibiotics to prevent infection.

In related embodiments, the catheter 1801 may have an on/off switch or valve 1813 accessible by the subject (activated by a magnet or by mechanical pressure) located on the subject's body such as on the skin or, when used in connection with fluid delivery to the inner ear, on the skull between the fluid delivery reservoir and intra inner ear section. The valve or switch 1813 may be used to prevent backflow of fluid. The catheter 1801 may additionally include a moveable stopper 1815 to promote ease and accuracy of insertion. The catheter 1801 is designed with an internal channel 1803 for fluid delivery. For example, localized delivery of fluid to the inner ear may maintain spiral ganglions cell functional characteristics, regenerate dendrites, and promote the preservation of residual hearing, arrest progressive hearing loss. Applications may include delivery of cortico-steroids to prevent inflammation, medicine to arrest sclerosis, and tissue growth and be used for the novel treatment for tinnitus and vertigo.

Fluid delivery is accomplished through the hollow channel 1803 formed on the catheter lead up to a location intra scala. One or more outlets 1809 may be included in the catheter 1801. The channel 1803 may be connected to an internal micro pump or to a port including a septum for external pumping of pharmacological agent. The hollow channel 1803 disposed close to the center or more off-centered to the edges of the catheter 1801 is formed by reverse molding. This means that a place holder may be included in a mold prior to injection molding. After injection molding, the place holder then is removed and a hollow channel is left in its place. Outlet(s) 1809 for the fluid delivery channel may be located basally and/or apically. The outlet(s) 1809 for fluid delivery may be coated with a ring of slow release bioactive agent to prevent tissue growth and occlusion of the outlets over time.

Each single outlet 1809 for fluid delivery may include two outlet channels 1817 and 1819 180 degrees apart. The two outlet channels 1817 and 1819 are connected either in a rectilinear fashion or they are offset from one another. The object of having the two outlet channels 180 degrees apart in a catheter designed for fluid delivery to the inner ear (as shown in FIG. 19) is to ensure that one outlet channel is always facing the perilymphatic fluid. With one outlet channel of the outlet 1809 facing the basilar membrane or the lateral wall of the scala tympani the possibility of the outlet channel becoming occluded exists. Each outlet channel may be formed with micromachined titanium and the metal laced with Cortico steroid-laced Silicone (drug eluting) covering (conformal coating, dipped, plasma deposition) on titanium micro tube. Such surface modification is intended to prevent occlusion of the outlets 1809.

Figure 20:
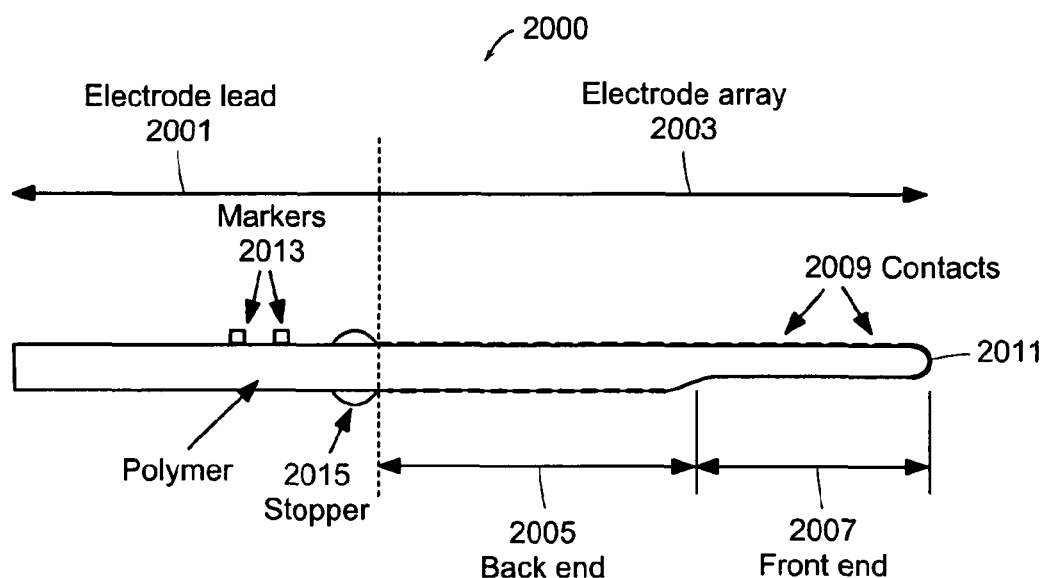
FIG. 20 is a graphical illustration of an implantable electrode in accordance with another embodiment of the invention.
Figure 21:
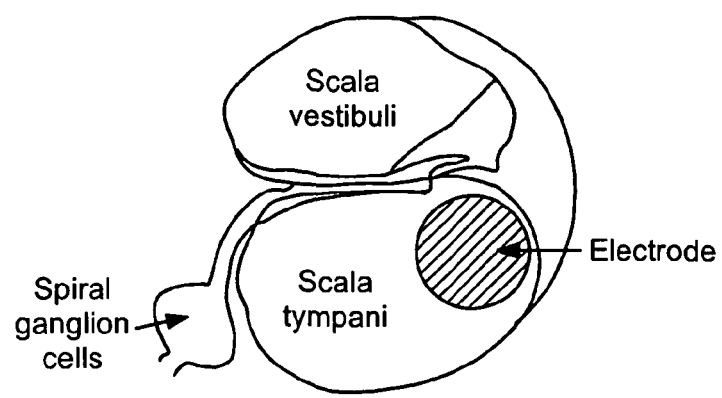
FIG. 21 is a graphical illustration of the electrode of FIG. 20 implanted in the inner ear of a subject.

FIG. 20 is a graphical illustration of an implantable electrode in accordance with another embodiment of the invention. The electrode 2000 comprises an electrode lead 2001 and an electrode array 2003. The electrode array 2003 includes a front end 2007 and a back end 2005. The electrode array 2003 is defined as the distance from the first contact 2009 on the front end 2007 to the last contact on the back end 2005. The electrode 2000 is made of a polymer with wires and contacts 2009 embedded or deposited on the polymer. The polymer may be silicone, fluoropolymer, or other biocompatible material. Most cochlear implant electrodes which have been designed for scala tympani lateral wall placement have a limited electrode extent of around 16 mm. Insertion depth of the electrode in the scala tympani is usually limited to around 23 mm. An electrode extent of 16 mm inserted 23 mm along the lateral wall of the scala tympani covers a limited sound frequency range and bandwidth in the cochlea. With the electrode partially displaced towards the medial wall, the frequency range increases but remains fractional of the full bandwidth since some electrodes are more or less close to the lateral wall. With an electrode extent of more than 26 mm inserted 28 to 31 mm along the outer wall the near complete bandwidth of the cochlear can be stimulated either at the spiral ganglion cells in the first cochlea turn, and/or at the axonal processes in the 2nd turn. With deep insertion, current spread is not required for stimulating tonotopic regions out of range of the 1st and last contact on the electrode array. A prerequisite to the benefits associated with deep electrode insertion is minimum insertion trauma from base to apex.

The electrode 2000 is designed to have properties which reduce the amount of force necessary for introduction in the cochlea. Reducing the electrode insertion force and increasing the electrode flexibility reduces the amount of trauma inflicted to the soft tissue which lines the scala tympani walls. Reducing the insertion trauma to the maximum is most beneficial to the patients who suffer from severe deafness and may be using a hearing aid in the ipsilateral ear, or have residual hearing which allows perception of low frequency sound unaided but have poor speech discrimination. The interest in keeping electrode trauma minimized is compounded by the fact that a patient implanted today may receive a device replacement or a device addition which restores some aspects of the degenerated neural pathway. If such neural a pathway is mechanically disturbed during electrode insertion there is a high likelihood that the pathway will be permanently destroyed.

A cochlear implant electrode is usually inserted through the inner ear (scala tymapani or scala vestibuli) through a hole drilled on the bony surface protecting the spiraling cochlea. If residual hearing is present it may be of interest to limit the insertion depth to a region below where acoustic hearing is present. A stopper 2015 on the electrode 2000 can limit insertion depth to a fixed predetermined value, 20 mm for example (but not limited to 20 mm) 20 mm corresponds to about 1 turn of cochlea. The stopper 2015 is designed to have vertical wall which prevents insertion beyond the cochleostomy. Slots may be built on the stopper 2015 to allow a surgeon to view the cochleostomy as the stopper 2015 approaches the external bone of the inner ear. In another embodiment, the stopper 2015 has a conical shape which allows for plugging of the cochleostomy. The stopper 2015 can also be a slider which is moved down from a superior region on the electrode 2000.

The insertion depth of the electrode 2000 may be controlled and limited to a pre-determined value. The predetermined insertion depth value may be based on the patient audiogram. If the audiogram indicates significant residual hearing (50 dB or more for example) up to 2000 Hz, the surgeon could choose to limit insertion depth to 16 mm. The limitation of the insertion depth may take place with the use of a pre-cut biocompatible and sterile tube inserted from the from end of the electrode down to the stopper 2015. A 4 mm long tubing of sufficient thickness in front of a 24 mm long electrode (length from electrode tip to stopper wall) would limit insertion depth to 20 mm.

What distinguishes the electrode 2000 from other designs is the presence of the front end 2007 and back end 2005 on the electrode array 2003. The front end 2007 is much thinner than the back end 2005. In one embodiment, the front end 2007 of the electrode 2000 covers ¼ to ½ of the electrode extent. The bulk mass of front end 2007 of the electrode 2000 may be about ½ the bulk mass of the back end. It is understood that in this design the electrode 2000 neither grows continuously, nor is of constant diameter or cross sectional shape along the electrode extent. Rather, the electrode 2000 includes a discontinuity in its cross sectional shape. The discontinuity defines the limit of front end 2007 and the beginning of the back end 2005 of the electrode array 2003. The front end 2007 is designed to have low insertion and low bending forces required to push the array around the coiling, upward spiral geometry of the scala tympani. The back end 2005 is designed to maximize the pushability of the electrode to achieve a deep insertion when required. Pushability is important for electrode design since an electrode with low pushability will collapse around the cochleostomy before able to impart a forward movement to the tip 2011 of the electrode. To favor the insertion of the electrode 2000, the tip 2011 of the device may be thin and rounded with no sharp edges. In addition the front end 2007 and the back end 2005 of the electrode array 2003 may be tapered. Tapered in this sense means that the cross sectional area of the front end 2007 and back end 2005 grows continuously.

On the electrode extent, eight or more contacts 2009 are embedded or deposited on the polymer substrate. At present, eight contacts 2009 are the minimum required to reach asymptotic performance in speech understanding for implanted patients. The contacts 2009 may be made of platinum (Pt), platinum iridium (PtIr), or iridium oxide. The contacts 2009 may be round or oval or may be rectangular shaped with rounded edges. Rounded edges reduce the current density at the edges of the electrode contact. Current density at the edge of the contact 2009 surface is usually responsible for the initial contact dissolution of the metallic surface. The contacts 2009 may be in the form of a spherical ball such as that produced by flaming the tip of a platinum iridium wire. Each of the contacts 2009 may be a single or paired contact. In one embodiment, a combination of paired and single contacts may be used. Contacts 2009 located on the back end 2005 are paired while contacts located on the front end 2007 are unpaired. In this manner the flexibility of the front end 2007 of the electrode is preserved while the pushability of the back end 2005 is maintained.

Figure 22:
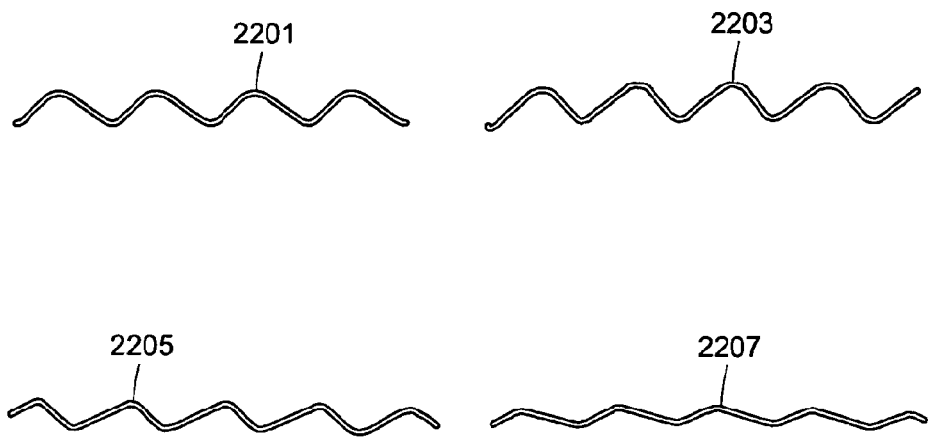
FIG. 22 is a pictorial illustration of wires associated with the electrode of FIGS. 20 and 21.

Each contact 2009 is electrically connected to an insulated wire (2201, 2203, 2205, or 2207, shown in FIG. 22) that runs through the polymer matrix forming the electrode 2000. The electrode wires 2201, 2203, 2205, or 2207 are thin down to 15 microns in diameter as thin wires reduce the insertion force. The wires 2201, 2203, 2205, or 2207 are preferably wiggled as shown in FIG. 22. Wiggled wires are much more flexible than straight wires and they require much less force to bend. The frequency and magnitude, and shape of the wiggled wires is adapted to minimize insertion forces.

Figure 23:
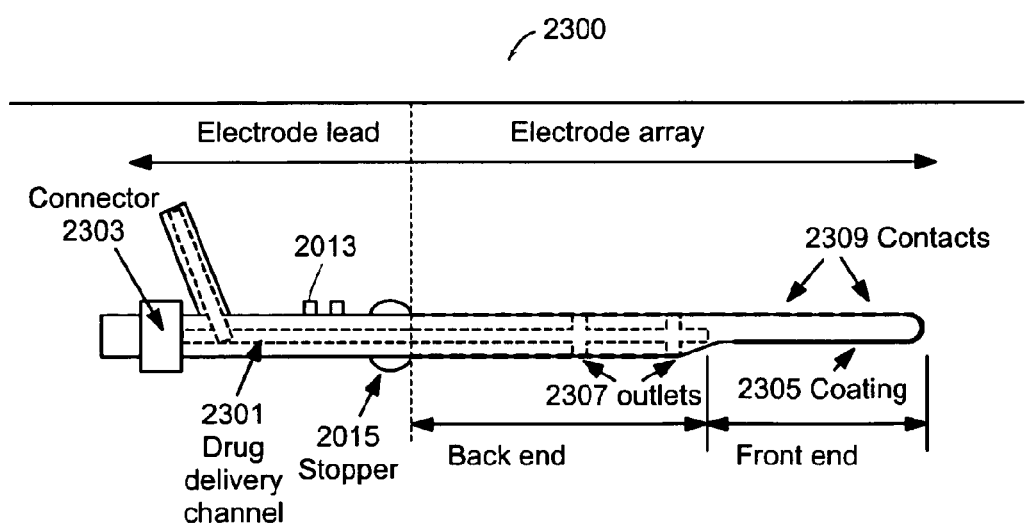
FIG. 23 is a graphical illustration of an implantable electrode for delivering fluid to the body of a subject in accordance with another embodiment of the invention.
Figure 24:
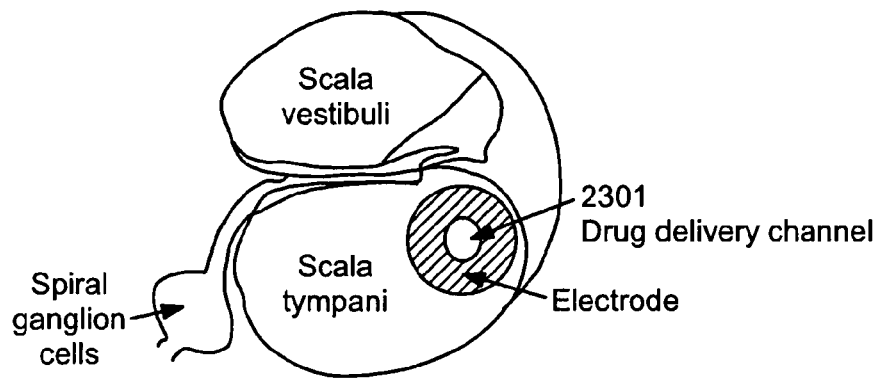
FIG. 24 is a graphical illustration of the electrode of FIG. 23 implanted in the inner ear of a subject in accordance with a further embodiment of the invention.

FIG. 23 is a graphical illustration of an implantable electrode array for delivering fluid to the body of a subject in accordance with another embodiment of the invention. In accordance with this embodiment, an implantable electrode 2300 is designed with an internal channel 2301 for fluid delivery. For example, localized delivery of fluids to the inner ear in the presence of a cochlear implant electrode (see FIG. 24) could maintain spiral ganglions cell count as well as functional characteristics, regenerate dendrites, and promote the preservation of residual hearing. Applications could include delivery of cortico-steroids to prevent inflammation and intra scala tissue growth as well as novel treatment for tinnitus and vertigo. The inclusion of a fluid delivery function with a cochlear implant is therefore a valuable aspect of cochlear implant design.

Fluid delivery is applied through a hollow channel 2301 formed on the electrode lead up to a location intra scala. One to several outlets 2307 may be included between or close to the electrode contacts 2309. The hollow channel 2301 may be connected to an internal micro pump or to a port including a septum for external pumping of pharmacological agent. The micro pump or the port may be located near the implant housing. The method for fabricating the hollow channel 2301 such that it is close to the center or more excentered to the edges of the electrode 2300 includes reverse molding. Again, in reverse molding, to form an internal hollow channel 2301, a place holder is included in the mold prior to injection molding. After injection molding the place holder is removed and a hollow channel is left in its place.

One or more outlets 2307 for the fluid delivery channel 2301 may be located near or in between basal contacts 2309 located on the electrode array 2303. The outlet(s) 2307 for fluid delivery may be coated with a ring of bioactive agent to prevent tissue growth and occlusion of the outlets over time.

Figure 25:
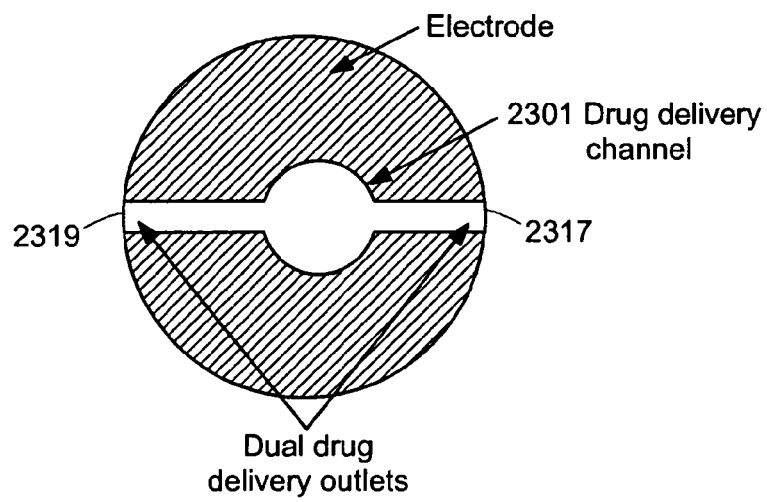
FIG. 25 is a graphical illustration of a cross sectional view of the electrode of FIG. 23.

FIG. 25 is a graphical illustration of the fluid delivery outlets of the electrode array of FIG. 23. Each single outlet 2307 for fluid delivery includes of two outlet channels 2317 and 2319 180 degrees apart. The two outlet channels 2317 and 2319 are connected either in a rectilinear fashion or they are offset but in each case they are 180 degrees apart. The object of having the two outlet channels 2317 and 2319 180 degrees apart in a electrode for a cochlear implant is to ensure that one outlet channel is always facing the perilymphatic fluid. With one outlet channel of the outlet 2307 facing the basilar membrane or the lateral wall of the scala tympani the possibility of the outlet channel becoming occluded exists. The fluid delivery outlets 2307 may be made of titanium or other metal coated with a pharmaceutical agent, including lubricating coating to prevent occlusion of the openings when the drug is not pumped through the channel 2301. The coated fluid delivery outlets 2307 are embedded into the silicone of the electrode.

Figure 26:
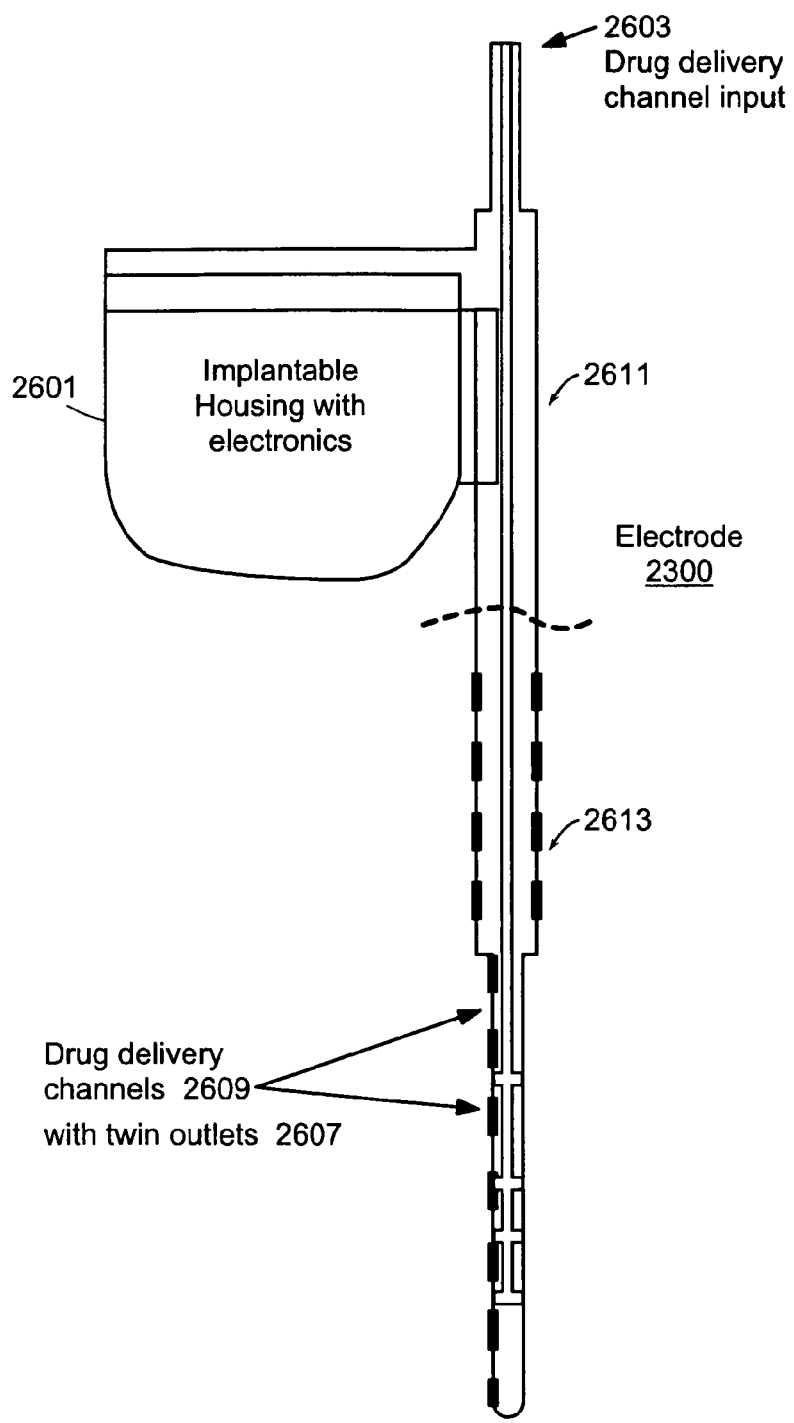
FIG. 26 is a graphical illustration of an electrode used in connection with an implantable housing in accordance with a further embodiment of the invention.
Figure 27:
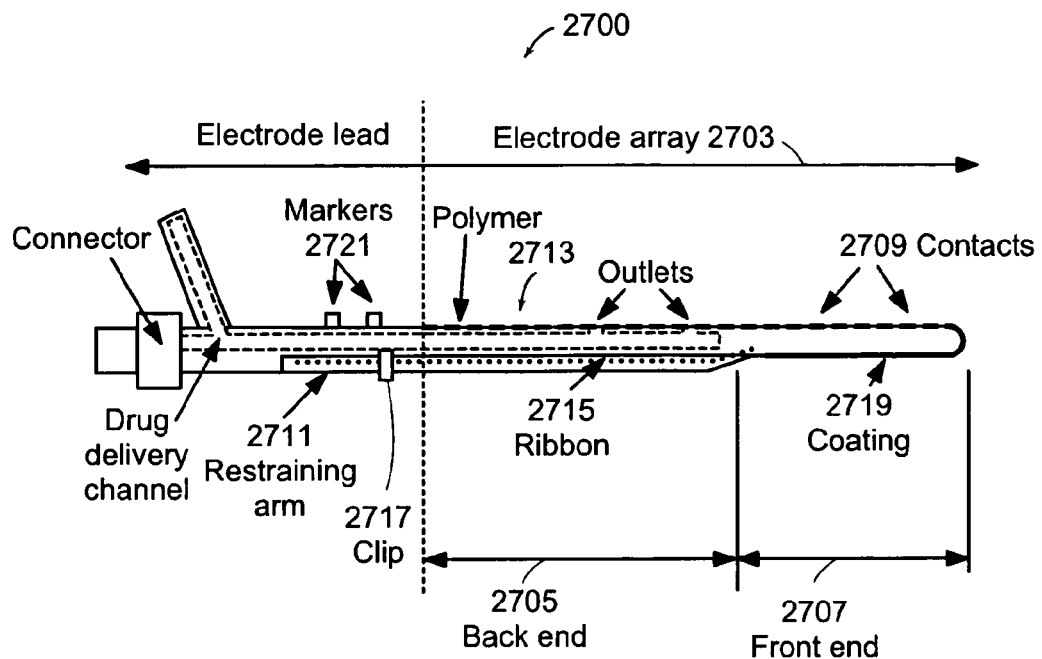
FIG. 27 is a graphical illustration of an implantable electrode in accordance with another embodiment of the invention.

FIG. 26 is a graphical illustration of an electrode for use in connection with an implantable prosthesis in accordance with a further embodiment of the invention. In accordance with this embodiment, the implant electrode 2600 includes an electrode array 2613 and an electrode lead 2611. The electrode lead 2611 is to be electrically connected to a metal or ceramic housing 2601 containing electronics. The electronics generate a current pulse to be delivered to the electrode contacts. The current pulse travels to the contacts via wires embedded in a polymer matrix. The electrode lead 2611 may optionally be terminated at a right angle.

Modeling of intra cochlear stimulation and animal EABR data indicates that an electrode array positioned close to the inner wall of the scala tympani would be beneficial to the neuro stimulation of cochlea implants. Such electrodes are referred to as perimodiolar electrode. There is a consensus that a perimodiolar electrode would lower psycho-acoustic threshold, increase the dynamic range of stimulation, and reduce channel interaction. Channel interaction may be caused by the field overlap from individual electrodes. Further potential benefits expected from a perimodiolar array include reduced power consumption to drive the implant, reduced side effects for the patient, implementation of innovative stimulation scheme, and better place coding of frequency. A larger number of electrodes may be effectively used.

FIGS. 27-30 illustrate of an implantable electrode array in accordance with another embodiment of the invention. In accordance with this embodiment, the electrode is designed to be displaced toward the inner wall of the scala tympani upward spiraling cavity as shown if FIG. 29. The front end 2707 of the electrode 2700 is unchanged from that described in accordance with FIG. 23. The front end 2707 of the electrode 2700 facilitates deep penetration of the scala tympani with minimum insertion forces. The back end 2705 of the electrode, however, is modified. The back end 2705 of the electrode 2700 is segmented in two parts that are joined together for insertion. After full insertion of the electrode 2700, the two segments 2711 and 2713 situated on the back end 2705 of the electrode array are disconnected by a pull back movement on the segment which comprises the electrode. In this embodiment, the two segments 2711 and 2713 remain connected at the junction of the front end 2707 and back end 2705 of the electrode 2700. When used with a cochlear implant, the two segments 2711 and 2713 also remain connected in a location in the middle ear. The two segments 2711 and 2713 are disconnected in between the two mentioned locations.

For clarity the two segments are referred to as the electrode branch 2713 and a restraining arm 2711. The two segments 2711 and 2713 are and remain connected during the whole insertion process. The preferred method of connecting the segments is via the pressure mating of a rail molded on the electrode branch 2713 with a slot molded on the restraining arm 2711. In a cochlear implant, segments 2711 and 2713 are latter disconnected for the positioning of a section of the electrode branch against or close to the modiolus. The cochlea from a human temporal bone with the electrode and restraining arm in position is shown on FIG. 29.

The restraining arm 2711 may include in its mass and along its whole length a platinum (Pt) or a platinum iridium (PtIr) ribbon or wire 2715, annealed or not annealed, to increases or decrease the rigidity of the restraining arm. Such control of the rigidity of the restraining arm 2711 is important in a cochlear implant to maintain good insertion properties (flexibility) as well as sufficient rigidity for when a retro positioning technique is applied to the electrode branch 2713 to displace the electrode branch 2713 closer to the modiolus. If the restraining arm 2711 is too soft, it will buckle during the retro-positioning technique.

Figures 28, 29:
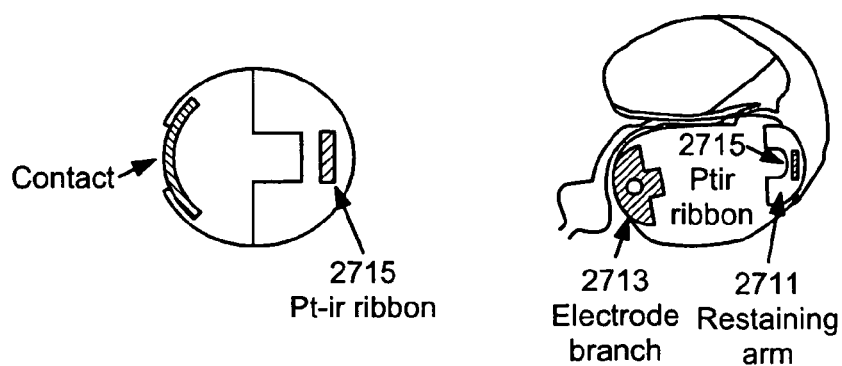
FIG. 28 is a graphical illustration of a cross sectional view of the electrode of FIG. 27.
FIG. 29 is a graphical illustration of the electrode of FIG. 27 implanted in the inner ear of a subject.
Figure 30:
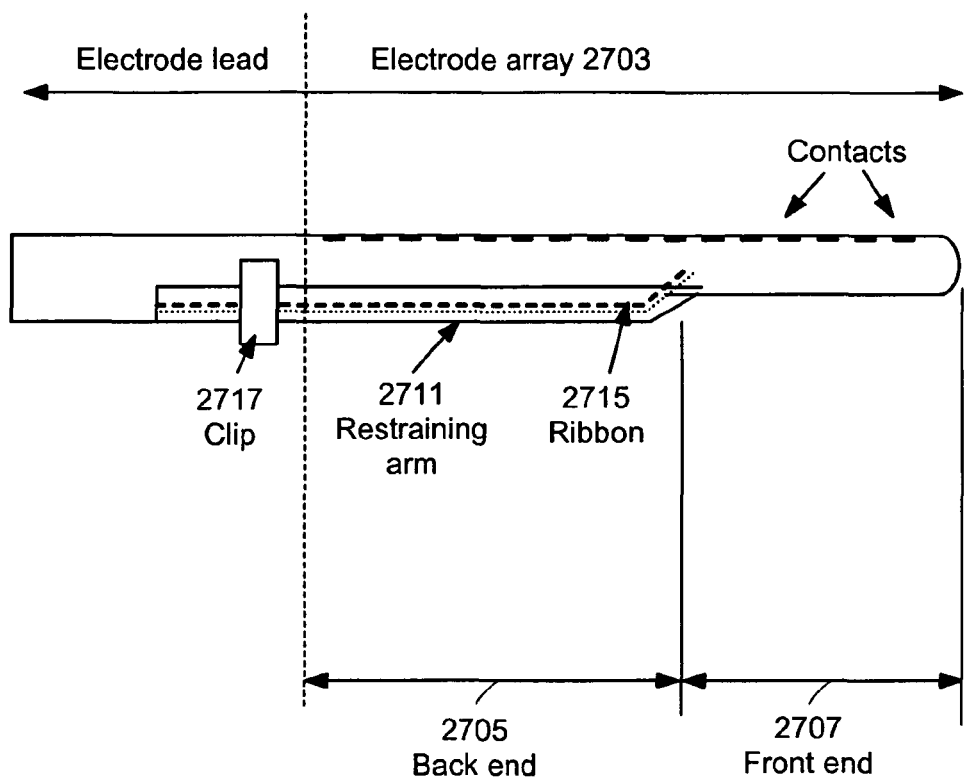
FIG. 30 is a graphical illustration of the electrode of FIG. 27 including a clip for joining the segments.

The shape of the ribbon 2715 may be that of a rectangle with a ratio of length to width of 2 to 1 (as shown in FIG. 28). The orientation of the ribbon 2715 may be such that the shorter length oriented medial to lateral (from outer wall-inner wall). Such an orientation of the ribbon 2715 in a cochlear implant facilitates the movement of the electrode array 2703 from the base of the scala toward the apex, while reducing movement of the array in the superior direction, toward the fragile tissue of the basilar membrane and organ of Corti. An added advantage of the rectangular shape of the ribbon 2715 is that it maintains the electrode contact facing the modiolus during insertion. The generally rectangular shape of the PtIr ribbon 2715 may have rounded angles to reduce any cutting into the silicone matrix, which form the restraining arm 2711. The metallic core of the restraining arm 2711 may be modified in all or in parts to increase flexibility or rigidity of the restraining arm 2711 in whole or in part as is deemed necessary to the invention. Modification of the ribbon 2715 may include but is not limited to, heat, chemical, and mechanical treatment of the metal. It is understood that the composition of the restraining arm 2711 is not limited to a combination of silicone and metal, and that other biocompatible polymer such as Teflon may be used in connection with the restraining arm concept.

When used with a cochlear implant, the electrode 2700 may be sequentially inserted, and then the electrode 2700 is positioned toward the inner wall. In a first phase, the electrode array 2703 with the two segments 2711 and 2713 connected is inserted along the outer wall of the scala tympani. In a second phase, the section of the back end 2705 of the electrode array 2703 corresponding preferably to the basal turn of the scala tympani is displaced to come close to or to connect with the inner wall of the same scala tympani. This section is now referred to as the perimodiolar section. The perimodiolar section corresponds preferably to the basal turn of the cochlear because this is where the majority of electro-excitable neural elements are situated. These neural elements (spiral ganglion cells) would benefit the most from more proximal electrode stimulation. The remaining intra cochlear section of the electrode branch 2713 is referred to as the deep insertion section. The deep insertion section is designed to be deeply inserted in the scala tympani but it is not positioned against the inner wall by any voluntary action.

Following the full insertion of the segmented electrode array 2703 into the scala tympani of the cochlea, the restraining arm 2711 is held stationary posterior to the cochleostomy (outside the cochlea) by the surgeon and with some micro-tool such as forceps or tweezers. The electrode branch 2713 is then unmated or disconnected from the restraining arm and retracted out of the scala. This slight pulling of the electrode array 2703 out of the cochlea effectively uncouples the electrode branch 2713 and the restraining arm 2711, except at the point where the two segments converge. It is important to note that at the convergence point the two segments are attached via a metallic rod or ribbon 2715 made of PtIr 80-20%, for example, such as that supplied by Medwire Sigmund Cohn Corp, Mount Vernon, N.Y. In one embodiment, the end of the wire or ribbon 2715 fits into a silicone hollow cavity on the electrode branch 2713. Key to the retro-positioning technique is the synergy between the less flexible ribbon 2715 and wire in the core of the restraining arm 2711 and the more flexible electrode branch 2713. An important element of the electrode 2700 is the segmented aspect of the electrode. Another substantial element of the design is the option to connect firmly the two segments 2711 and 2713 for ease of insertion. The firm and yet detachable connection may be established by several means. One means of segment connection is via a rail and a slot having matching dimensions. The electrode branch 2713 and restraining arm 2711 may be pressure mated during manufacturing. The mating of the silicone keeps the electrode and restraining arm connected during insertion.

Another means of connecting the two segments 2711 and 2713 is via an envelope design. If such a design is adopted, the envelope may be round or ellipsoid in shape. It is understood that the mating of the electrode is not restricted to the designs shown and that any mating which is profitable for the connection, insertion, disconnection, and positioning of the electrode is feasible. In accordance with yet another method, the two segments 2711 and 2713 may be connected with a hydrogel which dissolves in the fluid of the inner ear within a few minutes of insertion. The binding of two dissimilar silicones which are disconnectable may also connect the two segments.

The electrode segments 2711 and 2713 have a convergence point so that when the implant needs replacement, the two segments 2711 and 2713 of the electrode array 2703 should be easily disconnectable. In order to achieve disconnectability as well as restraining action during retro-positioning, the two segments 2711 and 2713 may be joined by a bare PtIr ribbon 2715 section, which comes out of the restraining arm 2711 and is lodged snugly or loosely in an oriented silicone cavity molded on the electrode branch 2713. In case of revision surgery, the two segments 2711 and 2713 can be dislocated at their point of convergence by pulling back on the restraining arm 2711 with sufficient force. The cavity may be parallel to the axis of the array or may be oriented in such a way as to provide resistance for retro-positioning. The ribbon or wire 2715, which is used as the spine of the restraining arm 2711, may be terminated as a ball to reduce sharp edges. The two segments 2711 and 2713 of the electrode array 2703 may be attached together outside the cochlea. Such attachment may be advantageous to prevent the movement of the electrode branch 2713 in relation to the restraining arm 2711. With respect to a cochlear implant, movement of the electrode branch 2713 post-operatively could lead to a release of the connection of the electrode branch 2713 with the modiolus. The in such an embodiment, the two segments 2711 and 2713 may be attached with a closable titanium clip 2717 seen more clearly in FIG. 30.

There are several advantages of the electrodes described above. First, in a cochlear implant, a section of the electrode may be deeply inserted in the cochlear, up to the apex, with minimized forces because of the front end design of the electrode. Additionally, a section of the electrode preferably corresponding to the first turn of the cochlear may be displaced toward to and up to the inner wall of the inner ear cavity. The two segments 2711 and 2713 of the electrode are and remain attached during the insertion process (but are disconnected during the positioning process, post insertion, and by voluntary action). The connection to the modiolus is independent of morphology and special tools are not required for insertion and positioning.

The front end 2707 of the electrode 2700, for up to a 15 mm length, may be coated with a thin biocompatible lubricating coating 2719. The coating 2719 may be permanent or biodegradable. Lubricating coating reduces the friction between the electrode and the tissue during insertion, therefore reducing insertion forces. Lubricating coating needs to be applied in a restricted front end length of the electrode so that instrument can hold the electrode and push in.

The electrode may also be equipped with a stopper (as show in FIGS. 20 and 23) located on the outer shell of the polymer electrode. The stopper 2015 is designed to prevent electrode insertion beyond a defined limit. The defined insertion limit is from 18 mm to 31 mm. The stopper 2015 may be made of a polymer material such as silicone, and preferably of the same material as the electrode. A polymer tube such as silicone can be inserted in front of the stopper 2015 to limit the electrode insertion to a pre-defined limit which may be adapted tot the audiogram of the individual patient. The shape of the stopper 2015 may be such that it allows the surgeon to see beyond the stopper 2015 through slits manufactured on the stopper 2015. Further, a marker 2721 may be placed on the electrode array 2703 toward the back of the array to indicate the direction of the contact line and to therefore indicate how to maintain the contact orientation once all contacts 2709 have disappeared in the cochlea.

In yet another embodiment, the implantable electrodes may have an impermeable connector (as at 2313 of FIG. 23 or 2723 of FIG. 27) between the distal and proximal end of the electrode. A connector is desirable since multiple re-implantations are likely to occur during the lifetime of the patient. Re-implantation is usually caused by electronic failures in the housing part of the implant and do not implicate the electrode itself. With respect to cochlear implants, each re-implantation with the removal of the electrode array from the inner ear is likely to inflict some additional damage and trauma to the internal tissue of the inner ear. Since trauma may be cumulative, inner ear function such as spiral ganglion cells and nerve tissue survival may decline over time. The use of an impermeable connector 2313 or 2723 suppresses cumulative trauma due to re-implantation since with a connector re-implantation only requires removal of the implantable electronics when such electronics failed. Such connector 2313 or 2723 is preferably located in the middle ear cavity or in the mastoidectomy. The connector 2313 or 2723 may also be placed on the surface of the skull close to the housing, which contains the encapsulated electronics. The connector 2313 or 2713 should be impermeable to fluid penetration. The function of impermeability may be brought about by pressure mating of a male and female connector or a flat bed connector. Impermeability may also be imparted by the use of a fast curing elastomer or other synthetic material pasted around the two connector parts. Curing causes sealing of the connector part and insulation from moisture. The connector ideally has as many leads as there are electrode channels. For a cochlear implant, the location of the connector 2313 or 2723 may be in the middle ear, in the mastoidectomy, or on the implant housing.

Figure 31:
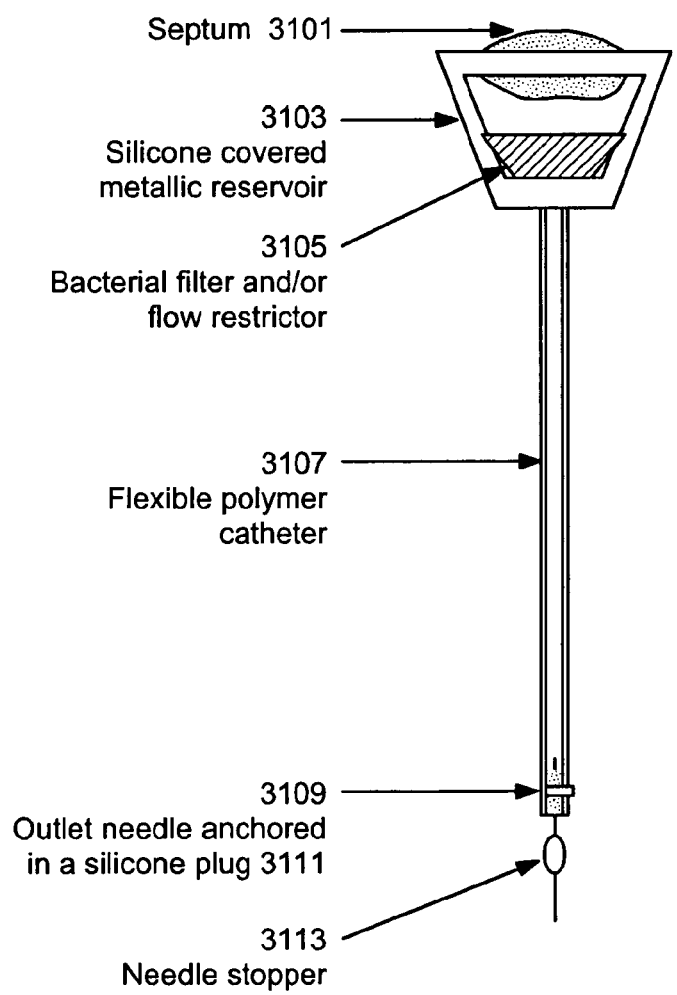
FIG. 31 is graphical illustration of an apparatus for delivering fluid to the body of a subject in accordance with a further embodiment of the invention.

FIG. 31 is graphical illustration of a further apparatus for delivering fluid to the body of a subject in accordance with a further embodiment of the invention. The apparatus includes a fluid reservoir 3103 with septum 3101 and a catheter 3107. The apparatus connects the inner surface of the skin of a human or animal subject with a fluid filled non-vascular organ in the human body and permits injection of fluids or pharmaceutical solutions topically to the particular organ though the flexible polymer catheter 3107 which is terminated by a metallic hollow needle 3109 (shown in detail in FIG. 32). The fluid reservoir 3103 and septum 3101 may be driven by an external or by an implantable pump. The apparatus may include a bacterial filter and/or flow restrictor 3105 disposed between the reservoir 3103 and catheter 3107. In accordance with a related embodiment, the apparatus may also include a donut or ringed shaped gold covered magnet (not shown) on the inner skin surface of the reservoir 3103 for positioning a needle on top of the septum 3101. Such a magnet may be encapsulated in a layer of silicone continuous with silicone covering the reservoir 3103. Further, the inner surface of the catheter 3107 and the exit needle 3109 may be coated with hydrophobic or hydrophilic conformal coating to prevent or restrict fibrous tissue growth and prevent biofilm formation. The exit needle 3109 may have an outlet at its tip or at its sides. Such an apparatus may be connected to the inner ear, the bladder, the stomach, or the intestines of a human or animal subject. When connected to the inner ear of a subject, the needle 3109 may be partially inserted in the posterior tympanotomy or in the mastoidectomy.

Figure 32:
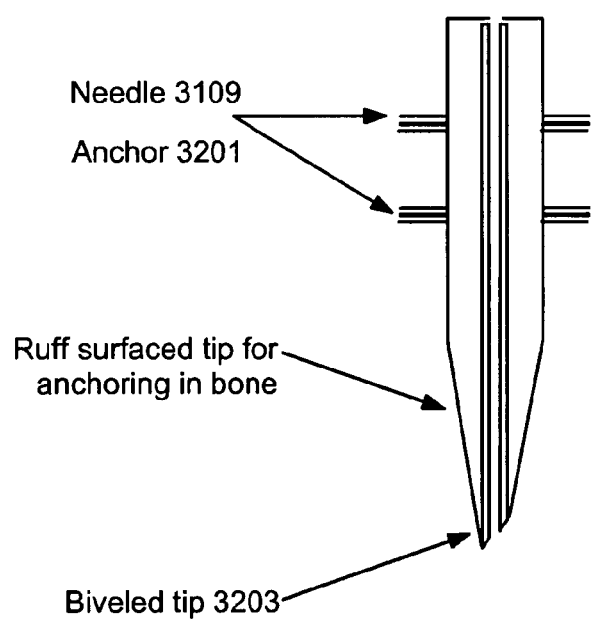
FIG. 32 is a graphical illustration of a needle of the embodiment of FIG. 31.

As noted above, the reservoir 3103 may be metallic and silicone covered. The reservoir may also be conically shaped and the septum 3101 may be disposed on the greater diameter of the cone. When connected to the inner ear of a subject, such a conically shaped reservoir should be of dimensions adequate to snugly fit in a mastoidectomy, such that the non-septum side of the reservoir 3103 is connected to a catheter 3107. The catheter 3107 terminates on the outer side of needle 3109. As shown in FIG. 32, the needle 3109 may be designed to be introduced on the promontory bone or in the semicircular canal of the inner ear after partial thinning of the bone. The needle 3109 may include a barbed outer surface and an anchoring device 3201 for providing bone anchoring. The needle 3109 may also include a conical stopper 3113 located at a short distance from the tip of the needle.

Figure 33:
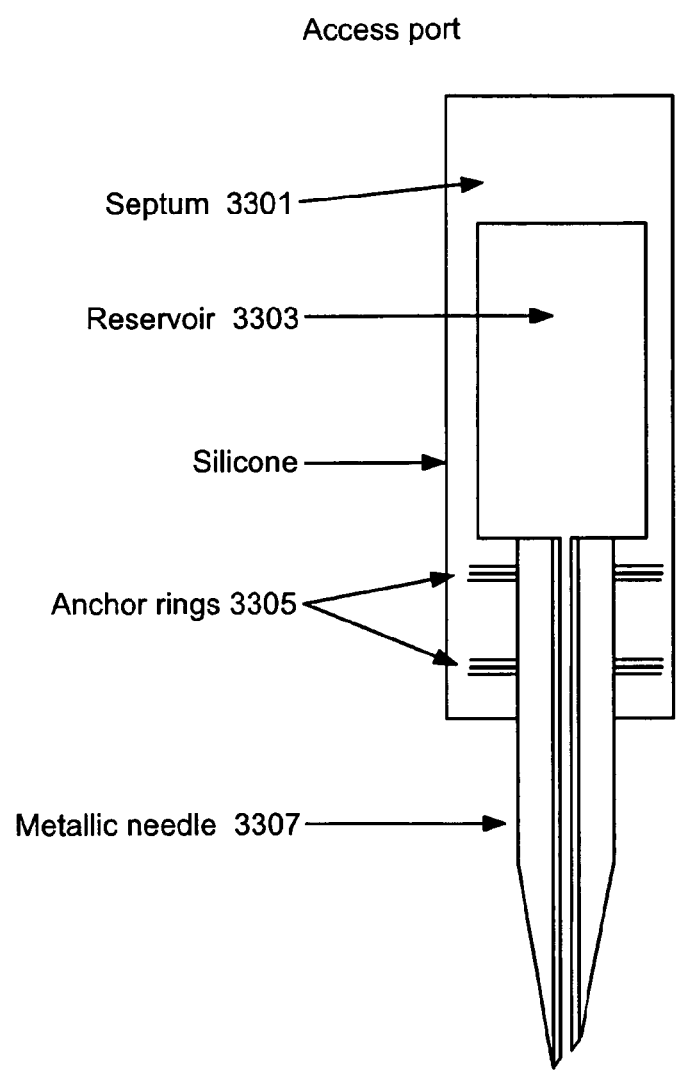
FIG. 33 is a graphical illustration of an implantable access port in accordance with another embodiment of the invention.

FIG. 33 is a graphical illustration of an implantable access port which may be used with the embodiments of FIGS. 31 and 32. The access port includes an input septum 3301 which may be made of compressed silicone, a micro-reservoir 3303 and a port needle 3307. The port needle 3307 may be anchored to the access port with metallic rings 3305 embedded in the silicone. The port needle 3307 may be partially covered with silicone and may have an outlet in its tip or in a side surface. The port needle 3307 may be introduced in the fluid of the inner ear after partial removal of the bony cover with a drill. In accordance with related embodiments, the port needle 3307 may be partially inserted in the posterior tympanotomy with the input septum 3301 and micro-reservoir 3303 in the mastoidectomy.

Figure 34:
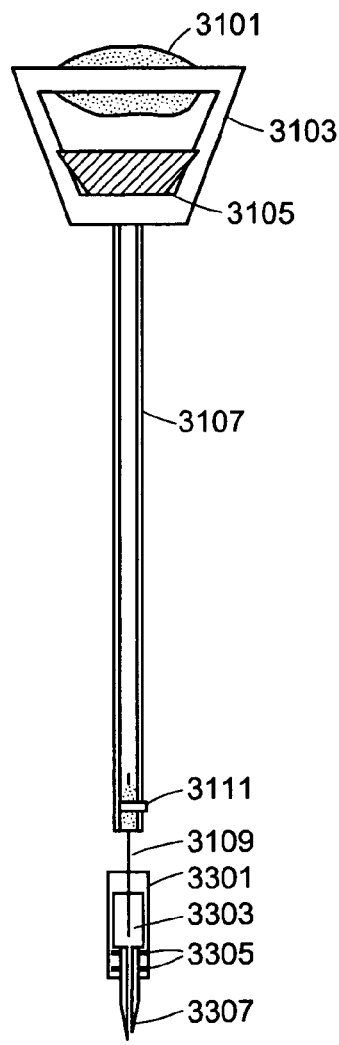
FIG. 34 is a graphical illustration of an apparatus for delivering fluid to the body of a subject in accordance with FIGS. 31-33.

FIG. 34 is a graphical illustration showing that the implantable access port may be connected to the apparatus described with respect to FIG. 31 and/or the needle described and shown in FIG. 32.

As noted above, the invention and its embodiments described herein are not limited to application to the inner ear. Other applications, such as anywhere in the body where it is desirable to have a pump and a delivery catheter with or without electrical stimulation, are also possible with the use of this connecting system. For instance, it may be that such a connection is made on or in the skull at a preferred location for fluid delivery to some location in the brain.

While the invention has been described in connection with specific embodiments thereof, it will be understood that it is capable of further modification. This application is intended to cover any variation, uses, or adaptations of the invention and including such departures from the present disclosure as come within known or customary practice in the art to which invention pertains.

What is claimed is:

1. An implantable drug delivery system comprising:
 a middle ear section having:
  a proximal end adapted to be fixed to a tympanic membrane of a patient,
  a distal end penetrating through a fluid-tight sealed opening into the inner ear of the patient;
  a hollow interior between and connecting the proximal end and the distal end, and
  an outer surface enclosing the hollow interior and sealed to prevent leakage between the hollow interior and the middle ear of the patient; and
 an inner ear section having:
  a proximal end connected to the distal end of the middle ear section at the sealed opening,
  a closed distal end terminating the inner ear section some predetermined distance within the cochlea,
  a hollow interior configured for containing a replaceable pharmaceutical agent, and
  an outer surface configured to release the pharmaceutical agent from the hollow interior into the inner ear of the patient,
 whereby the middle ear section and the inner ear section are configured to cooperate for replacing the pharmaceutical agent through the proximal end of the middle ear section to the inner ear section.

2. The implantable drug delivery system according to claim 1, further comprising:
 a micro-valve configured to provide a secure path through the sealed opening.

3. The implantable drug delivery system according to claim 1, wherein the inner ear section is made of a polymer matrix material.

4. The implantable drug delivery system according to claim 1, wherein the inner ear section is an electrode array of a cochlear implant system.

\* \* \* \* \*